United States Patent
Min et al.

(10) Patent No.: US 9,752,190 B2
(45) Date of Patent: Sep. 5, 2017

(54) COMPOSITION FOR DETECTING UNDIFFERENTIATED HUMAN PLURIPOTENT STEM CELL, MONOCLONAL ANTIBODY 6-1 AND USE THEREOF

(71) Applicant: Korea Research Institute of Bioscience and Biotechnology, Daejeon (KR)

(72) Inventors: Jeong Ki Min, Daejeon (KR); Jongjin Park, Daejeon (KR); Kwang-Hee Bae, Daejeon (KR); Sang Chul Lee, Daejeon (KR); Yee Sook Cho, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 99 days.

(21) Appl. No.: 14/806,514

(22) Filed: Jul. 22, 2015

(65) Prior Publication Data
US 2016/0097096 A1 Apr. 7, 2016

(30) Foreign Application Priority Data

Aug. 12, 2014 (KR) .................. 10-2014-0104464
Jul. 14, 2015 (KR) .................. 10-2015-0099600

(51) Int. Cl.
*C07K 16/28* (2006.01)
*C12Q 1/00* (2006.01)
*G01N 33/50* (2006.01)
*C12Q 1/68* (2006.01)
*G01N 33/569* (2006.01)

(52) U.S. Cl.
CPC ............ *C12Q 1/6881* (2013.01); *C07K 16/28* (2013.01); *G01N 33/56966* (2013.01); *C12Q 2600/158* (2013.01); *G01N 2333/705* (2013.01); *G01N 2400/00* (2013.01)

(58) Field of Classification Search
None
See application file for complete search history.

(56) References Cited

U.S. PATENT DOCUMENTS 8,323,966 B2 * 12/2012 Lebkowski .......... C12N 5/0623
435/325

OTHER PUBLICATIONS

Badcock, et al. (1999) "The Human Embryonal Carcinoma Marker Antigen TRA-1-60 Is a Sialylated Keratan Sulfate Proteoglycan," Cancer Research 59:4715-4719.
Fukuda et al. (2006) "Fluorescence-Activated Cell Sorting-Based Purification of Embryonic Stem Cell-Derived Neural Precursors Averts Tumor Formation after Transplantation," Stem Cells 24:763-771.
Kannagi et al. (1983) "Stage-Specific Embryonic Antigens (SSEA-3 and -4) are Epitopes of a Unique Globo-Series Ganglioside Isolated from Human Teratocarcinoma Cells," EMBO Journal 2(12):2355-2361.
Takahashi et al. (2007) "Induction of Pluripotent Stem Cells from Adult Human Fibroblasts by Defined Factors," Cell 131:861-872.
Dongho Choi et al. (2005) "In Vitro Differentiation of Mouse Embryonic Stem Cells: Enrichment of Endodermal Cells in the Embryoid Body," Stem Cells, 23:817-827.

* cited by examiner

*Primary Examiner* — Elly-Gerald Stoica
(74) *Attorney, Agent, or Firm* — Lathrop & Gage LLP

(57) ABSTRACT

The present invention relates to a composition for detecting the undifferentiated human pluripotent stem cells comprising an agent useful for measuring the level of Desmoglein 2 (Dsg 2) mRNA or the protein thereof, a kit for detecting the undifferentiated human pluripotent stem cells comprising the said composition, a method for detecting the undifferentiated human pluripotent stem cells containing the step of measuring the level of Desmoglein 2 mRNA or the protein thereof, a method for evaluating the differentiation of human pluripotent stem cells and thereafter for separating the undifferentiated human pluripotent stem cells, a method for reducing the undifferentiated status of human pluripotent stem cells by inhibiting the expression or activation of Desmoglein 2, and a monoclonal antibody binding specifically to human Desmoglein 2.

5 Claims, 18 Drawing Sheets

Figure 1A
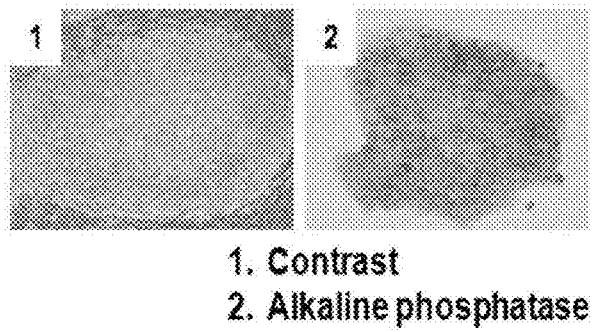
1. Contrast
2. Alkaline phosphatase
Figure 1B
Figure 1C
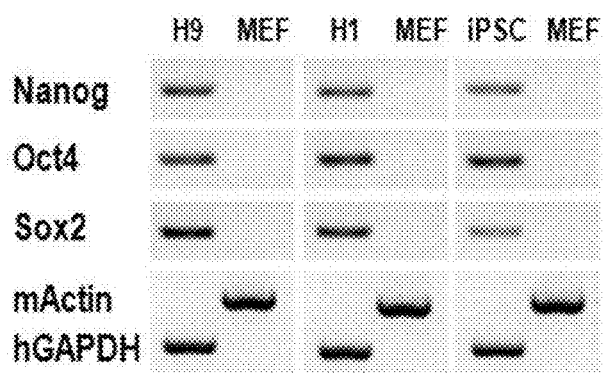
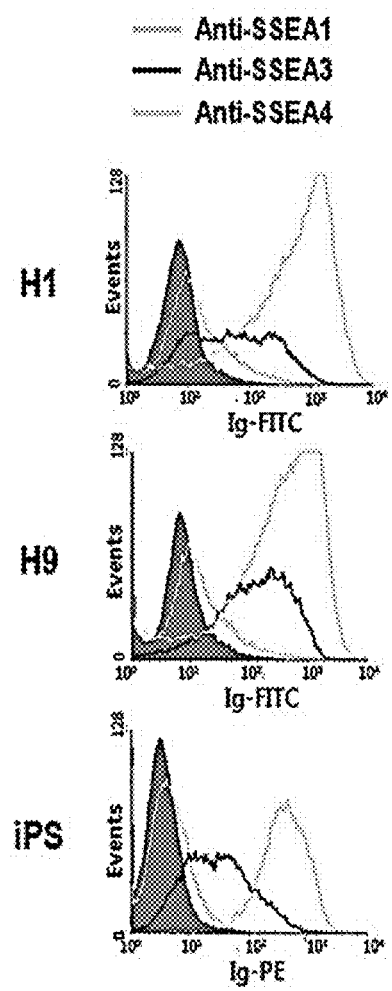

Figure 4A

```
   1 MARTRDRVRL LLLICFNVG SGLHLQVLST RNENKLLPKH PHLVRQKRAW
  51 ITAPVALREG EDLSKKNPIA KIHSDLAEER GLKITYKYTG KGITEPPFGI
 101 FVFNKDTGEL NVTSILDREE TPFFLLTGYA LDARGNVEK PELIKVLD
 151 INDNEPVFTQ DVFVGSVEEL SAAHTLVMKI NATDADEPNT LNSKISYRIV
 201 SLEPAYPPVF YLNKDTGEIY TTSVTLDREE HSSYTLTVEA RDGNGEVTDK
 251 PVKQAQVQIR ILDVNDNPPV VENKVLEGMV EKNQVNEYT RIKVFDADEI
 301 GSDNWLANFT FASGNEGGYF HIETDAQTNE GIVTLIKEVD YEEMKNLDFS
 351 VIVANKAAFH KSIRSKYKPT PIPRVKVKN VKEGHFKSS VISIYVSESM
 401 DRSSKGQID NFQAFDEDTG LPAHARYVKL EDRDNWISVD SVTSEIKLAK
 451 LPDFESKYVQ NGTYTVKIVA ISEDYPEKTI TGTVLINVED INDNCPTLIE
 501 PVQTICHDAE YVNVTAEDLD GHPNSGPFSF SVIDKPPGMA EKWKIARGES
 551 TSVLLQQSEK KLGRSEIQFL ISDNQGFSCP EKQVLTLTVC EVLHGSGCRE
 601 AQHDSYVGLG PAAIALMILA FLLLLVPLL FLPVDKGGSL VGHNGVGGMA KAFTPIPGTI
 651 EMLHPWNNEG APPEDKVVPS FLPVDKGGSL VGHNGVGGMA KEATMKGSSS
 701 ASIVKGQHEM SEMDGRWEEH RSLLSGRATQ PTGATGAINT TETTKTARAT
 751 GASIDMAGAQ AAAVALNEEF LRNTPTDKAA SYTEEDENHT AKDCLLVYSQ
 801 EETESLNASI GCCSFEGEL DDRFLDDLGL KFKTLAEVCL GQKIDINKD
 851 EQKQKPATET SMNTASHSLC EQTMVNSENT YSSGSSFPVP KSLQEANAEK
 901 VTQEIVTERS VSSRQAKYA TPLPDPMASR NVATETSTV TGSTMPPTTV
 951 ILGPSQPSL IVTERVYAPA STLVDQPYAN EGTVVTERV IQPHCGSNP
1001 LEGTQHLQDV PYVHVRERES FLAPSSGVQP TLAMPNIAVG QNVTVTERVL
1051 APASTLQSSY QIPPTENSMTA RNTTVSGAGV IQPLPDFGLE EGHSNSTIT
1101 TSSTRVTKHS TVQHSYS
```

Figure 4B

Heavy Chain 6-1 subgroup I

```
CAG GTT AAG CTG CAG GAG TCT GGG CCT GAG CTG GTG AGG CCT GGG GAA TCA GTG AAG
Gln Val Lys Leu Gln Glu Ser Gly Pro Glu Leu Val Arg Pro Gly Glu Ser Val Lys
                         CDR1
ATT TCC TGC AAG GGT TCC GGC TAC ACA TTC ACT GAT TAT GCT ATG CAC TGG GTG AAG
Ile Ser Cys Lys Gly Ser Gly Tyr Thr Phe Thr Asp Tyr Ala Met His Trp Val Lys
                                                     CDR2
CAG AGT CCT GCA AAG ACT CTA GAG TGG CTT GGA GTT ATT AGT ATT TAC TAT GAT AAT
Gln Ser Pro Ala Lys Thr Leu Glu Trp Leu Gly Val Ile Ser Ile Tyr Tyr Asp Asn

ACA AAC TAC AAC CAG AAA TTT AAG GGC AAG GCC ACA TTG ACT GTT GAC AAA TCC TCC
Thr Asn Tyr Asn Gln Lys Phe Lys Gly Lys Ala Thr Leu Thr Val Asp Lys Ser Ser

AGC ACA GCC TAT ATG GAA CTT GCC AGA TTG ACA TCT GAG GAT TCT GCC ATC TAT TAC
Ser Thr Ala Tyr Met Glu Leu Ala Arg Leu Thr Ser Glu Asp Ser Ala Ile Tyr Tyr
              CDR3
TGT GCA AGA GAG GGT GAC TAC TTT GCT TTG GAC TAC TGG GGT CAA GGA ACC TCA GTC
Cys Ala Arg Glu Gly Asp Tyr Phe Ala Leu Asp Tyr Trp Gly Gln Gly Thr Ser Val

ACC GTC TCC TCA GCC AAA ACG ACA CCC CCA TCT GTC TAT - 381
Thr Val Ser Ser Ala Lys Thr Thr Pro Pro Ser Val Tyr - 127
```

Figure 7

Light Chain 6-1 subgroup I
GAT ATT GTG ATG ACA CAG TCT CCA GCA ATC ATG TCT GCA TCT CCA GGG GAG AAG GTC
Asp Ile Val Met Thr Gln Ser Pro Ala Ile Met Ser Ala Ser Pro Gly Glu Lys Val
                        CDR1
ACC ATG ACC TGC AGT GCC AGC TCA AGT GTA AGT TAC ATG TAC TGG TAC CAG CAG AAG
Thr Met Thr Cys Ser Ala Ser Ser Ser Val Ser Tyr Met Tyr Trp Tyr Gln Gln Lys
                                                CDR2
CCA GGA TCC TCC CCC AGA CTC CTG ATT TAT GAC ACA TCC AAC CTG GCT TCT GGA GTC
Pro Gly Ser Ser Pro Arg Leu Leu Ile Tyr Asp Thr Ser Asn Leu Ala Ser Gly Val CCT GTT CGC TTC AGT GGC AGT GGG TCT GGG ACC TCT TAC TCT CTC ACA ATC AGC CGA
Pro Val Arg Phe Ser Gly Ser Gly Ser Gly Thr Ser Tyr Ser Leu Thr Ile Ser Arg
                                            CDR3
ATG GAG GCT GAA GAT GCT GCC ACT TAT TAC TGC CAG CAA TGG AGT AGT TTC CCG CTC
Met Glu Ala Glu Asp Ala Ala Thr Tyr Tyr Cys Gln Gln Trp Ser Ser Phe Pro Leu

ACG TTC GGT GCT GGG ACC AAG CTG GAG CTG AAA CGG GCT GAT GCT GCA CCA ACT GTA
Thr Phe Gly Ala Gly Thr Lys Leu Glu Leu Lys Arg Ala Asp Ala Ala Pro Thr Val

TCC - 345
Ser - 115

Figure 8

ComPOSITION FOR DETECTING UNDIFFERENTIATED HUMAN PLURIPOTENT STEM CELL, MONOCLONAL ANTIBODY 6-1 AND USE THEREOF

CROSS-REFERENCE TO RELATED APPLICATIONS

This application claims the benefit of South Korean Application No. 10-2014-0104464, filed on Aug. 12, 2014, and South Korean Application No. 10-2015-0099600, filed on Jul. 14, 2015, both of which are incorporated by reference in their entireties.

BACKGROUND OF THE INVENTION

1. Field of the Invention

The present invention relates to a composition for detecting the undifferentiated human pluripotent stem cells comprising an agent useful for measuring the level of Desmoglein 2 (Dsg2) mRNA or the protein thereof, a kit for detecting the undifferentiated human pluripotent stem cells comprising the said composition, a method for detecting the undifferentiated human pluripotent stem cells containing the step of measuring the level of Desmoglein 2 mRNA or the protein thereof, a method for evaluating the differentiation of human pluripotent stem cells and thereafter for separating the undifferentiated human pluripotent stem cells, a method for reducing the undifferentiated status of human pluripotent stem cells by inhibiting the expression or activation of Desmoglein 2, and a monoclonal antibody conjugating specifically to human Desmoglein 2.

2. Description of the Related Art

Stem cell is the cell that has a potential for unlimited proliferation as remains undifferentiated status and is capable of being differentiated into a specific cell with a unique function and shape once certain environment and conditions are given. Human pluripotent stem cell is a self-renewal cell in a certain in vitro culture condition. Owing to its characteristics of being differentiated into almost every cell forming a living subject, it has been an important target of study not only to understand basic knowledge on the development, differentiation, and growth of a subject but also to develop an agent for cell therapy which is believed to be a fundamental treatment method for the damage or injury of a subject or for various diseases, to screen a various novel drug candidates and their medicinal effects, to disclose a cause of disease, and to develop a treatment method, etc.

One of the pluripotent stem cells, embryonic stem cell, unlike the differentiated cell arrested in the cell cycle, can produce the same cell as itself by cell division, which is called self-renewal. Embryonic stem cell displays pluripotency that is the ability to be differentiated into almost every functional cell in human body under a certain environment or stimulus. So, it is expected to induce the differentiation of the embryonic stem cell into a specific target cell when a specific cell or organ is damaged by accident or disease. Accordingly, the treatment method using the embryonic stem cell rises as a fundamental treatment method for various incurable diseases.

Human induced pluripotent stem cell (iPSC) is also one of those pluripotent stem cells, that induces pluripotency of the cell that has been finished with differentiation so as to make the cell to be re-differentiated again. This stem cell also has the self-renewal ability like embryonic stem cell, indicating that this stem cell can also be able to be differentiated into almost every kind of cell. According to the reports made so far, human induced pluripotent stem cell has similar characteristics in gene expression and differentiation capability to pluripotent embryonic stem cell (Takahashi, K et al., Cell, 131:861-872, 2007).

To obtain the cells differentiated from human pluripotent stem cells, human pluripotent stem cells are first induced to be differentiated into a specific type of cells; and then the differentiated cells are conjugated with surface markers for recognition; and then the recognized cells are separated by FACS (Fluorescent Activated Cells Sorter) (Fukuda, H et al., Stem Cells (2006) (24.3: 763-771)), or the differentiated cells are labeled with antibody and then the labeled cells are separated by MACS (Magnetic Activated Cell Sorting) (David, R et al., Stem Cells (2005) (23.4: 77-82)). MACS is known to outperform FACS since it can eliminate the risk of cell exposure on laser necessary for FACS.

In the method for obtaining the differentiated cells, either the cell separation is performed by FACS or by MACS, the possibility of mixed-existence with undifferentiated pluripotent stem cells is not completely excluded, suggesting that both methods are limited in separating the differentiated cells alone with 100% purity. That is, the differentiated cells originated from pluripotent stem cells might be mixed with the undifferentiated cells, and there might be a risk of the undifferentiated pluripotent stem cells to cause a tumor called teratoma, which has been a continuous issue in the development of cell therapy products. Therefore, it is requested to develop a novel method to eliminate selectively the undifferentiated cells having the risk of causing teratoma alone with leaving the differentiated cells.

Recently, Oct-4, Nanog and Sox-2, which are involved in self-renewal and pluripotency, have been used as intracellular markers for the separation of human pluripotent stem cells. TRA-1-60, TRA-1-81, SSEA3, and SSEA4 antibodies have been used as cell surface markers, however the most of molecules recognized by these antibodies have carbohydrate epitope or have the functions that are not necessary for self-renewal or pluripotency of human pluripotent stem cell (Badcock, et al., Cancer Res. 59:4715-4719, 1999; Kannagi et al., EMBO. J. 2:2355-2361, 1983; Brimble et al., Stem Cells. 25:54-62, 2007). Therefore, it is necessary to develop cell surface markers that are expressed in human pluripotent stem cells in order to study or separate the undifferentiated human pluripotent stem cells. Likewise, a novel agent that can recognize specifically human pluripotent stem cells and accordingly can be used efficiently to eliminate the undifferentiated human pluripotent stem cells during cell therapy is highly requested.

Under these circumstances, the present inventors tried to develop a novel method and technique to detect and separate specifically the undifferentiated human pluripotent stem cells. As a result, the inventors identified Desmoglein 2 which is specifically expressed in the undifferentiated human pluripotent stem cells and thereafter prepared an agent that can be conjugated specifically to the undifferentiated pluripotent stem cells, and further confirmed that the detection and separation of the undifferentiated human pluripotent stem cells could be achieved by this method by using the agent, leading to the completion of this invention.

SUMMARY OF THE INVENTION

It is an object of the present invention to provide a composition for detecting the undifferentiated human pluripotent stem cells comprising an agent for measuring the level of Desmoglein 2 (Dsg 2) mRNA or the protein thereof.

It is another object of the present invention to provide a method for detecting the undifferentiated human pluripotent stem cells containing the step of measuring the level of Desmoglein 2 mRNA or the protein thereof in the separated human pluripotent stem cells.

It is also an object of the present invention to provide a method for evaluating the differentiation of human pluripotent stem cells containing the step of measuring the level of Desmoglein 2 mRNA or the protein thereof in the separated human pluripotent stem cells.

It is further an object of the present invention to provide a method for separating the undifferentiated human pluripotent stem cells comprising the following steps:

(a) reacting human pluripotent stem cells with an agent specifically binding to Desmoglein 2 protein; and (b) separating the human pluripotent stem cells that has been conjugated with the said agent.

It is also an object of the present invention to provide a method for reducing the undifferentiated status of human pluripotent stem cells containing the step of treating an agent that can reduce the expression or activation of Desmoglein 2 to the separated human pluripotent stem cells.

It is also an object of the present invention to provide a monoclonal antibody that is specifically binding to Desmoglein 2.

It is also an object of the present invention to provide a polynucleotide encoding the said monoclonal antibody, an expression vector containing the polynucleotide, and a transformant harboring the said expression vector.

It is also an object of the present invention to provide a method for eliminating the undifferentiated human pluripotent stem cells containing the step of reacting human pluripotent stem cells with an agent that is specifically binding to Desmoglein 2 protein.

To achieve the above objects, the present invention provides a composition for detecting the undifferentiated human pluripotent stem cells comprising an agent for measuring the level of Desmoglein 2 (Dsg 2) mRNA or the protein thereof. Particularly, the agent included in the composition is to measure the level of Dsg2 protein expressed on cell surface.

In this invention, the term "human pluripotent stem cell" indicates the cell that has self-renewal capacity and thus is capable of being differentiated into almost every kind of cells forming a living body, which includes embryonic stem cell and induced pluripotent stem cell.

The "human pluripotent stem cell" can include the undifferentiated human embryonic stem cell existing in early embryonic blastocyst or epiblast and the differentiated human cell such as human induced pluripotent stem cell that has been reversely differentiated to have pluripotency from germ cell, somatic cell, or precursor cell, but not always limited thereto.

In this invention, the term "Desmoglein 2 (Dsg2) protein" is a kind of Desmoglein protein which is a transmembrane glycoprotein existing in desmosome. Desmoglein protein has three kinds of molecules, which are Dsg1, Dsg2, and Dsg3. Dsg1 and Dsg3 are mainly expressed in stratified epithelium, and are known as the molecules targeting pemphigus, a kind of autoimmune skin disease. Dsg2 is known as a marker molecule of desmosome, but it is not confirmed yet whether or not Dsg2 can be used as a marker molecule of the undifferentiated human pluripotent stem cell.

In a preferred embodiment of the present invention, it was confirmed that the antibody prepared in this invention (named 6-1) was conjugated to the undifferentiated human embryonic stem cells (FIG. 2). To investigate the antigen to which the antibody of the present invention could be bound, the antibody conjugated protein was separated by immunoprecipitation and identified by mass spectrometry. As a result, it was confirmed that the protein conjugated with the antibody 6-1 was Desmoglein 2 (FIG. 4). It was also confirmed that Desmoglein 2 was expressed in the undifferentiated human pluripotent stem cells like other undifferentiation markers Nanog, Oct4, and Sox2, but was down-regulated in differentiated embryoid body (EB) (FIG. 10). The inventors confirmed from the above results that Desmoglein 2 protein was a marker expressed on the surface of the undifferentiated human pluripotent stem cells and the undifferentiated human pluripotent stem cells could be separated by using the Desmoglein 2 specific antibody.

Particularly, the agent for measuring the level of Desmoglein 2 mRNA can contain a set of primers or probe that specifically binds to the said gene.

In this invention, the term "primer" indicates a single-stranded oligonucleotide that can be used as a start point of template-directed DNA synthesis under proper conditions (4 different nucleoside triphosphates and polymerase) in an appropriate buffer. The preferable length of the primer depends on temperature and can vary according to a purpose of use, but generally the length of 15~30 nucleotide long is preferred. The sequence of the primer does not necessarily contain a perfectly complementary sequence to a part of the template sequence and such complementarity that allows the primer to be hybridized with the template and therefore allows the primer to carry its own function would be enough.

Therefore, the "primer set" of the present invention does not have to have completely homologous sequence with the nucleotide sequence of Desmoglein 2, the template, and only needs such complementarity that is enough to let the primer be hybridized and work therein. So, the primer sequence of the invention can contain RNA sequence. The primer can be designed by those in the art by referring the nucleotide sequence of the template polynucleotide sequence. For example, the primer can be designed by the primer design program such as PRIMER 3, VectorNTI, etc. The primer can be hybridized or annealed to a part of the template to form double-stranded structure.

In this invention, the "probe" can be a polynucleotide, the polynucleotide complement, the polynucleotide fragment, or the polynucleotide fragment complement. The probe can also be a material for being hybridized with the homologous DNA included in the sample, which is DNA, RNA, cDNA, or mRNA, and if it is DNA, it can be an oligomer. The probe can contain the repeated sequence in the nucleotide sequence 85% at highest, and preferably 70%, and more preferably 50%, and most preferably 40% herein. The size of the probe can be the total length of the above gene, or when an oligomer is used as the probe, its preferable length is 20~200 bp and more preferably 20~100 bp. When cDNA or RNA is used as the probe, its preferable length is 30~150 bp, but not always limited thereto, and the length and the material can be selected according to the purpose of use.

The probe can contain a detectable marker. The detectable maker can be any chemical moiety that is traced by any means known to those in the art. The detectable marker can be any moiety that can be detected by spectroscopy, photochemistry, or any biochemical, immunochemical, or chemical method. The method for labeling the nucleic acid probe is properly selected by considering the type and the location of marker, and the type of probe. The marker is exemplified by enzyme, enzyme substrate, radio-isotope, fluorescent dye, chromophores, chemiluminescent label, electrochemical luminescent label, ligand having a specific binding partner, and other markers capable of increasing, modifying, or reducing the detection signal strength by reacting to a target.

Particularly, the probe of the invention can be Desmoglein2 gene, the fragment of Desmoglein 2 gene, nucleic acid originated from the said Desmoglein 2 gene, or the fragment of the nucleic acid that can display any change in the expression in the undifferentiated human pluripotent stem cells and the differentiated cells as well, and at this time, the nucleic acid can be DNA or RNA.

The agent that is used to measure the protein level above can be an antibody specific to the said protein. The antibody specifically binding to Desmoglein2 protein is one or more antibodies selected from the group consisting of monoclonal antibody, chimeric antibody, humanized antibody, and human monoclonal antibody. At this time, the antibody can be a full length antibody or an antibody fragment. The antibody fragment herein can be Fab, F(ab'), F(ab')2 or Fv, but not always limited thereto. The antibody useful for measuring the level of Desmoglein2 protein can be the antibody 6-1 of the present invention, but not always limited thereto.

The term "protein level" in this invention indicates the level of protein that is expressed from gene in cells. Observing the protein level can overcome the limit of the study targeting mRNA with which the direct relation between the protein and mRNA in cells might not be disclosed. In this invention, the detection of the undifferentiated human pluripotent stem cell could be easily accomplished by observing the expression level of Desmoglein 2 protein.

The term "antibody" in this invention indicates an antigen specific protein molecule. Considering the purpose of the invention, the antibody herein indicates the antibody binding specifically to Desmoglein2 protein, the marker protein, which can include a monoclonal antibody, a polyclonal antibody, and a recombinant antibody. As explained hereinbefore, a full length antibody and an antibody fragment can also be included.

The monoclonal antibody can be prepared by the conventional well-known method using hybridoma (Kohler and Milstein (1976) European journal of Immunology 6:511-519) or using phage antibody library (Clarkson et al, Nature, 352:624-628, 1991; Marks et al, J. Mol. Biol., 222:58, 1-597, 1991). In general, hybridoma cells secreting monoclonal antibody can be made by fusion of cancer cell line with the immune cells obtained from an immunologically appropriate host animal, such as the mouse injected with an antigen protein. The fusion of such two different cell groups can be performed by the method well-informed to those in the art by using polyethyleneglycol and the antibody producing cells can be proliferated by the standard culture method. Subcloning is performed by limited dilution to obtain a uniform cell group. Then, the hybridoma cells that can produce antigen specific antibody are mass-cultured in vitro or in vivo.

It is easily understood by those in the art that the monoclonal antibody of the invention can be easily converted into chimeric antibody, humanized antibody, and human monoclonal antibody whose immunogenicity has been reduced in order for such monoclonal antibody to adapt to human body. The chimeric antibody, humanized antibody, and human monoclonal antibody are easily constructed from the monoclonal antibody of the invention by the well-known method, for example by transplanting the variable region of the monoclonal antibody of the invention, particularly complementarity determining region (CDR) or selectivity determining residue (SDR) of CDR into human antibody. These variants are also included in the scope of the present invention.

The polyclonal antibody can be prepared by the method well-informed to those in the art, for example by the following steps: injecting the said protein antigen into an animal; and obtaining the serum containing the antibody by blood-work. The polyclonal antibody can be produced from any random host animal including goat, rabbit, sheep, monkey, horse, pig, cow, and dog, etc.

Further, the antibody of the present invention can be either the complete full length antibody comprising two full length light chains and two full length heavy chains or the functional fragment of the antibody molecule. The functional fragment of the antibody molecule indicates the fragment that has at least antigen-binding capacity, which is exemplified by Fab, F(ab'), F(ab')$_2$ and Fv.

To measure the expression level of Desmoglein2 in the undifferentiated human pluripotent stem cells by using the said antibody, any method that is useful for measuring the production of antigen-antibody complex after treating the said antibody can be used without limitation.

The said "antigen-antibody complex" herein indicates the complex wherein Desmoglein 2 protein is conjugated with the antibody specific thereto. The antigen-antibody complex can be quantified by measuring the size of the detection label signal.

For example, the antigen-antibody complex can be quantified by Western blotting, ELISA (enzyme linked immunosorbent assay), immunoprecipitation assay, complement fixation assay, flowcytometry, or the method using protein chip, but not limited thereto.

In a preferred embodiment of the present invention, in order to produce the undifferentiated human pluripotent stem cell specific monoclonal antibody, the human pluripotent stem cell line H9 was treated with collagenase IV to inactivate the said stem cells. Then, the inactivated stem cells were intraperitoneally injected into the Balb/c mouse, leading to the immunization. The spleen cells obtained from the mouse were fused with NS1 myeloma cell line to obtain hybridoma, from which monoclonal antibody 6-1 was separated and purified. The binding capacity of the antibody to human pluripotent stem cell was investigated (FIG. 2A). As a result, the antibody was confirmed to bind neither to mouse embryonic stem cells (J1) nor to mouse embryonic fibroblasts (MEF) (FIG. 2B).

Particularly, the antibody can contain the heavy chain variable region ($V_H$) comprising (i) the complementarity-determining region (referred as "CDR" hereinafter) 1 represented by SEQ. ID. NO: 60, the heavy chain CDR2 represented by SEQ. ID. NO: 61, and the heavy chain CDR3 represented by SEQ. ID. NO: 62; and the light chain variable region ($V_L$) comprising the light chain CDR1 represented by SEQ. ID. NO: 64, the light chain CDR2 represented by SEQ. ID. NO: 65, and the light chain CDR3 represented by SEQ. ID. NO: 66. More particularly, the antibody can contain the heavy chain variable region represented by SEQ. ID. NO: 59 and the light chain variable region represented by SEQ. ID. NO: 63, but not always limited thereto. In this invention, the antibody comprising the heavy chain variable region represented by SEQ. ID. NO: 59 and the light chain variable region represented by SEQ. ID. NO: 63 was named the antibody '6-1'. As described hereinabove, the antibody can be the full length antibody or the fragment of the antibody, but not always limited thereto.

In a preferred embodiment of the present invention, the present inventors analyzed the nucleic acid sequence and amino acid sequence of the monoclonal antibody 6-1 secreted from the hybridoma prepared by the inventors in order to analyze the sequences of CDR1, CDR2, and CDR3 of the heavy chain variable region and the sequences of CDR1, CDR2, and CDR3 of the light chain variable region (FIG. 7 and FIG. 8).

As stated in scientific references, one or two CDRs can be omitted for antibody binding (Padlan et al., FASEB Journal 9: 133-139 (1995); Vajdos et al., Journal of Molecular Biology, vol. 320, pp. 415-428 (2002); Iwahashi et al., Mol. Immunol. 36:1079-1091, (1999); Tamura et al, Journal of Immunology, 164:1432-1441 (2000)). So, one or more CDR residues can be replaced in the said antibody or one or more CDRs can be omitted from the antibody. In fact, such replacement or exclusion is not limited as long as the Desmoglein2 protein binding capacity of the antibody remains.

The present invention also provides a kit for detecting the undifferentiated human pluripotent stem cells comprising the above composition.

The kit of the present invention can contain not only an agent that can measure the expression level of Desmoglein 2 protein in the undifferentiated human pluripotent stem cells but also one or more compositions, solutions, or devices appropriate for the analysis of the expression level. For example, the kit can contain a substrate, a proper buffer, a detection marker labeled secondary antibody, and a chromogenic substrate for the immunological detection of an antibody.

In addition, the kit can be used for Western blotting, ELISA (enzyme linked immunosorbent assay), immunoprecipitation assay, complement fixation assay, flowcytometry, or protein chip assay. At this time, the kit can additionally contain any additional composition or device to meet the requirement of each analysis method above. The detection of the undifferentiated human pluripotent stem cells can be achieved by comparing the production of antigen-antibody complex through the above methods.

The present invention also provides a method for detecting the undifferentiated human pluripotent stem cells containing the step of measuring the level of Desmoglein 2 mRNA or the protein thereof in the separated human pluripotent stem cells. Particularly, the measurement of the level of Desmoglein 2 protein of human pluripotent stem cells can be achieved by using the Desmoglein2 protein specific antibody.

The antibody was the same as described above. More particularly, the antibody can contain the heavy chain variable region ($V_H$) comprising the complementarity-determining region represented by SEQ. ID. NO: 59; and the light chain variable region ($V_L$) comprising the amino acid sequence represented by SEQ. ID. NO: 63. The detection of the undifferentiated human pluripotent stem cells can be achieved by measuring the level of Desmoglein2 protein by using the said antibody.

The present invention also provides a method for separating the undifferentiated human pluripotent stem cells comprising the following steps:
(a) reacting human pluripotent stem cells with an agent specifically binding to Desmoglein 2 protein; and
(b) separating the human pluripotent stem cells that has been conjugated with the said agent.

In the above method, the step of separating the human pluripotent stem cells can be achieved by flowcytometry, but not always limited thereto, and any conventional method well accepted by those in the art can be used.

In a preferred embodiment of the present invention, the inventors confirmed Desmoglein 2 as a marker that can be expressed specifically in the undifferentiated human pluripotent stem cells (FIGS. 3~5). The inventors further confirmed that the detection and separation of the undifferentiated human pluripotent stem cells could be succeeded by using the binding activity between Desmoglein 2 and the monoclonal antibody 6-1.

The present invention also provides a method for evaluating the differentiation of human pluripotent stem cells containing the step of measuring the level of Desmoglein 2 mRNA or the protein thereof in the separated human pluripotent stem cells. Particularly, the measurement of the level of Desmoglein 2 protein in the human pluripotent stem cells can be achieved by using the Desmoglein2 protein specific antibody or the antibody fragment binding thereto.

The antibody was the same as described above. More particularly, the antibody can contain the heavy chain variable region ($V_H$) comprising the amino acid sequence represented by SEQ. ID. NO: 59; and the light chain variable region ($V_L$) comprising the amino acid sequence represented by SEQ. ID. NO: 63.

In a preferred embodiment of the present invention, the sequence of the monoclonal antibody 6-1 that was specifically bound to Desmoglein2 was analyzed (FIG. 7 and FIG. 8). As a result, AP positive reaction was only confirmed in the colony distributed with those cells expressing Desmoglein2 (FIG. 11C), and the expressions of the undifferentiation markers Nanog, Oct4, and Sox2 were also confirmed (FIG. 11D). So, the differentiation of human pluripotent stem cells could be confirmed by measuring the expression level of Desmoglein 2.

The present invention also provides a method for reducing the undifferentiated status of human pluripotent stem cells containing the step of treating an agent that can reduce the expression or activation of Desmoglein 2 to the separated human pluripotent stem cells.

In a preferred embodiment of the present invention, shDsg2 was treated to the human pluripotent stem cells to inhibit the expression of Desmoglein 2. At this time, changes in the undifferentiated status of human pluripotent stem cells were observed and AP positive reaction was weakened (FIG. 12B). In the meantime, the expression of a pluripotency marker was reduced in Desmoglein 2 knock-down human pluripotent stem cells but at the same time the expression of a differentiation marker was increased. Also, p21, the cell cycle inhibitor, was increased (FIG. 12D). Therefore, it was confirmed that the undifferentiation status of human pluripotent stem cells was reduced when Desmoglein 2 was inhibited.

The agent that can reduce the expression or activation of Desmoglein 2 mRNA above can be an oligonucleotide inhibiting the expression of Desmoglein2 mRNA or an antibody inhibiting the activation of Desmoglein 2 protein, or a fragment of the said antibody, and further an antisense oligonucleotide, a siRNA oligonucleotide, an antibody, a single-stranded variable region fragment, a peptide, an aptamer, a low molecular compound, or a natural extract, but not always limited thereto.

Particularly, the said agent can be the antisense oligonucleotide or the siRNA oligonucleotide that can specifically bind to Desmoglein 2 mRNA, but not always limited thereto.

In this invention, the term "antisense oligonucleotide" indicates DNA or RNA containing the oligonucleotide sequence complementary to a specific mRNA or a derivative thereof, which acts to inhibit the translation of mRNA into protein by binding to the complementary sequence of mRNA. The antisense sequence against Desmoglein 2 is complementary to Desmoglein 2 mRNA and can be DNA or RNA sequence that can bind to Desmoglein 2 mRNA, which is able to inhibit the translation of Desmoglein 2 mRNA, translocation into cytoplasm, maturation, or other essential activities of biological functions.

Modification is allowed in the said antisense oligonucleotide to increase the effect thereof, for example one or more nucleotides, sugars, or backbones can be modified (De Mesmaeker et al., Curr Opin Struct Biol., 5(3):343-55 (1995)). The oligonucleotide backbone can be modified by phosphorothioate, phosphotriester, methyl phosphonate, single-stranded alkyl, cycloalkyl, single-stranded heteroatomic, and heterocyclic intersugar linkages. The antisense oligonucleotide can also contain one or more substituted sugar moieties. The antisense oligonucleotide can contain a modified nucleotide, which is exemplified by hypoxanthine, 6-methyladenine, 5-me pyrimidine (particularly 5-methylcytosine), 5-hydroxymethylcytosine (HMC), glycosyl HMC, gentobiosyl HMC, 2-aminoadenine, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine.

The antisense oligonucleotide of the present invention can be chemically conjugated with one or more moieties or conjugates in order to improve the activity and cell adsorbability of the antisense oligonucleotide. The said moieties are exemplified by such fat-soluble moieties as cholesterol moiety, cholesteryl moiety, cholic acid, thioether, thiocholesterol, aliphatic chain, phospholipid, polyamine, polyethylene glycol chain, adamantane acetate, palmityl moiety, octadecylamine, and hexylamino-carbonyl-oxycholesterol moiety, but not always limited thereto. The method for preparing the oligonucleotide containing such fat-soluble moiety is well known to those in the art (U.S. Pat. Nos. 5,138,045, 5,218,105, and 5,459,255). The modified oligonucleotide has increased stability to nuclease and increased binding affinity to the target mRNA.

The antisense oligonucleotide can be synthesized in vitro by the conventional method and then introduced into a living body or it can be synthesized in vivo. To synthesize the antisense oligonucleotide in vitro, RNA polymerase I is used. To synthesize the antisense RNA in vivo, the antisense RNA is transcribed by using a vector whose origin of MCS is on the opposite direction. It is preferred for such antisense RNA to contain translation stop codon in the sequence so as not to continue the translation into the peptide sequence.

The antisense oligonucleotide usable in this invention can be designed by referring the human Desmoglein2 mRNA sequence informed to those in the art. For example, the antisense oligonucleotide can be designed with the complementary sequence to human Desmoglein 2 mRNA CDS (coding sequence), the complementary sequence to starting codon and the surrounding sequence thereof, the complementary sequence to 5'-UTR, and the complementary sequence to 3'-UTR.

In this invention, the term "siRNA" indicates an oligonucleotide molecule mediating RNA interruption or gene silencing. Since siRNA can inhibit the expression of a target gene, it can be useful for efficient gene knock-down or gene therapy. The said siRNA was first found in plants, insects, fruit flies, and parasites. It is now applied to study on mammal cells.

The siRNA used in this invention can have the double-stranded structure wherein the sense strand that is the corresponding sequence to Desmoglein 2 mRNA is located on the opposite side of the antisense strand that is the complementary sequence to Desmoglein 2 mRNA, or can have the single-stranded structure which comprises the self-complementary sense and antisense strand.

The siRNA herein is not limited to the authentic, complete paring of double-stranded RNA region (a pair of RNAs) but also includes unpaired RNA region by mismatch (the corresponding sequence is not complementary) or bulge (chain on one side is left without being conjugated with matching nucleotides). Particularly, the siRNA that is complementary to the sequence in human Desmoglein 2 ORF start codon area can be constructed, which is of 10~100 nucleotides in length, preferably 15~80 nucleotides, and more preferably 20~70 nucleotides.

The siRNA terminal structure can be either blunt or cohesive. As long as the terminal structure can inhibit the expression of Desmoglein 2 gene via the effect of RNA interference (RNAi), the structure is not limited either to blunt or to cohesive. And the cohesive terminal structure can be either 3'-end protruding structure or 5'-end protruding structure.

The siRNA molecule of the present invention can have the insertion with a short nucleotide sequence (for example approximately 5~15 nt) in between the self-complementary sense and the antisense strand. At this time, the siRNA molecule formed by the expression of the nucleotide sequence can have the hairpin structure by intramolecular hybridization and as a result, the stem-and-loop structure is formed. This stem-and-loop structure is processed in vitro or in vivo to produce the active siRNA molecule that can mediate RNAi.

In this invention, the Desmoglein 2 activity inhibitor can be a Desmoglein 2 specific antibody, an antigen binding fragment of the Desmoglein 2 specific antibody, a peptide, an aptamer, a low molecular compound, or a natural extract, but not always limited thereto. The antibody or its antigen binding fragment is described hereinbefore.

In this invention, the term "peptide" indicates a linear or circular, preferably a linear molecule that is formed by the peptide bond among the amino acid residues. The peptide of the present invention can be prepared by the well informed chemical synthesis method, particularly by solid-phase synthesis techniques.

The peptide that can inhibit the activity of Desmoglein 2 by binding specifically to Desmoglein 2 can be prepared by the conventional method well informed to those in the art, for example by phage display. The peptide is composed of 4~40 amino acid residues, preferably 5~30, more preferably 5~20, and most preferably 8~15 amino acid residues, but not always limited thereto.

The stability of the peptide of the present invention could be improved by modifying amino acid residues. For example, one or more amino acid residues of the amino acid sequence of the peptide, particularly Gly residue, acetyl group, fluorenyl methoxy carbonyl group, formyl group, palmitoyl, myristyl group, stearyl group, or polyethyleneglycol (PEG) can be conjugated in N-terminal, and more particularly Gly residue can be conjugated in order to increase the stability of the peptide.

In this invention, the term "aptamer" indicates an oligonucleotide molecule having the binding activity to a certain target molecule. The said aptamer can inhibit protein activity by binding the certain target molecule, specifically via three-dimensional binding with the target protein. The aptamer of the present invention can be RNA, DNA, modified oligonucleotide, or a mixture thereof, and can be in the form of a linear chain or a ring.

The length of the aptamer of the invention is not limited, and is generally 15~200 nucleotide long. However, the aptamer is suggested to be composed of up to 100 nucleotides, preferably up to 80 nucleotides, and more preferably up to 60 nucleotides, and most preferably up to 45 nucleotides.

The aptamer of the present invention can have the modification of sugar residue (for example, ribose) of each nucleotide in order to increase the binding capacity, stability, and drug delivery capability, etc. The modified region can be 2', 3', and/or 4' site of the sugar residue, and the modification is the replacement of oxygen atom in that site with another atom. The modification is exemplified by fluorination, O-alkylation (for example, O-methylation, O-ethylation), O-allylation, S-alkylation (for example, S-methylation, S-ethylation), S-allylation, and amination (for example, —NH). Such modification of the sugar residue can be performed by the conventional method well known to those in the art (for example, Sproat et al., Nucle. Acid. Res. 1991 19, 733-738; Cotton et al., Nucl. Acid. Res. 1991 19, 2629-2635).

To increase the binding capacity of the aptamer of the invention, an oligonucleotide base (for example, purine, pyrimidine) can be modified (for example, chemically substituted). This modification is exemplified by 5-pyrimidine modification, 6- and/or 8-purine modification, exocyclic amine modification, 4-thiouridine substitution, and 5-bromo or 5-iodouracil substitution.

Also, the phosphate group in the aptamer of the invention can be modified to make the aptamer have resistance against nuclease and hydrolysis. For example, P(O)O group can be substituted with any of P(O)S (thioate), P(S)S (dithioate), P(O)NR$_2$ (amidate), P(O)R, R(O)OR', CO or CH$_2$ (formacetal) or 3'-amine (—NH—CH$_2$—CH$_2$—). At this time, each R or R' is independently H or substituted or non-substituted alkyl (methyl or ethyl). The linkage herein is exemplified by —O—, —N— or —S—. SO, the said modified group can be connected to the neighboring nucleotide by one of these linkages.

The modification herein also includes 3' and 5'-modification such as capping. The modification can also be achieved by adding such materials as polyethyleneglycol, amino acid, peptide, inverted dT, oligonucleotide, nucleoside, Myristoyl, Lithocolic-oleyl, Docosanyl, Lauroyl, Stearoyl, Palmitoyl, Oleoyl, Linoleoyl, other lipids, steroid, cholesterol, caffeine, vitamin, pigment, fluorescein, anticancer agent, toxin, enzyme, isotope, and biotin to the terminal. Such modification is explained in U.S. Pat. Nos. 5,660,985 and 5,756,703.

The present invention also provides a monoclonal antibody composed of the heavy chain variable region (V$_H$) comprising (i) the complementarity-determining region (referred as "CDR" hereinafter) 1 represented by SEQ. ID. NO: 60, the heavy chain CDR2 represented by SEQ. ID. NO: 61, and the heavy chain CDR3 represented by SEQ. ID. NO: 62; and the light chain variable region (V$_L$) comprising the light chain CDR1 represented by SEQ. ID. NO: 64, the light chain CDR2 represented by SEQ. ID. NO: 65, and the light chain CDR3 represented by SEQ. ID. NO: 66.

In a preferred embodiment of the present invention, the inventors confirmed that the protein which the monoclonal antibody 6-1 recognized and bound to was Desmoglein 2 (FIG. 4 and FIG. 5), and performed FACS to investigate the differentiated human pluripotent stem cells by using the antibody 6-1. As a result, it was confirmed that the expression of the human pluripotent stem cell undifferentiation marker SSEA3 was reduced and at the same time the expression of Dsg2 recognized by the antibody 6-1 was also rapidly decreased (FIG. 9A). When retinoic acid that was the material to induce differentiation was treated thereto, the binding capacity of the antibody 6-1 was reduced in the differentiated cells (FIG. 9C). Therefore, it was confirmed that Desmoglein 2 which was recognized by the monoclonal antibody 6-1 constructed in this invention was expressed specifically in the undifferentiated human pluripotent stem cells and the detection or separation of the undifferentiated human pluripotent stem cells expressing Desmoglein 2 was accomplished by recognizing thereof.

The present invention also provides a polynucleotide encoding the said monoclonal antibody, an expression vector comprising the said polynucleotide, and a transformant containing the said expression vector.

The said monoclonal antibody is as explained hereinbefore.

The polynucleotide encoding the monoclonal antibody is not limited as long as the polynucleotide can encode the monoclonal antibody composed of the heavy chain variable region (V$_H$) comprising (i) the complementarity-determining region (referred as "CDR" hereinafter) 1 represented by SEQ. ID. NO: 60, the heavy chain CDR2 represented by SEQ. ID. NO: 61, and the heavy chain CDR3 represented by SEQ. ID. NO: 62; and the light chain variable region (V$_L$) comprising the light chain CDR1 represented by SEQ. ID. NO: 64, the light chain CDR2 represented by SEQ. ID. NO: 65, and the light chain CDR3 represented by SEQ. ID. NO: 66. For example, the polynucleotide represented by SEQ. ID. NO: 67 that encodes the heavy chain variable region and the polynucleotide represented by SEQ. ID. NO: 68 that encodes the light chain variable region can be used, but not always limited thereto. In addition, considering the codon degeneracy or the preference of codon to be expressed in a host living subject to express the polynucleotide in the host, various modifications or transformations are allowed as long as they do not cause any change in the amino acid sequence of the polypeptide.

The expression vector containing the polynucleotide encoding the monoclonal antibody provided in this invention is not limited, and can be any expression vector that can duplicate and/or express the said polynucleotide in prokaryotic or eukaryotic cells including mammal cells (for example, cells of human, monkey, rabbit, rat, hamster, mouse, etc.), plant cells, yeast cells, insect cells, or bacteria cells (for example, *E. coli*, etc). Preferably, this expression vector is operably linked to a proper promoter in order to express the said nucleotide in host cells and at this time it can contain at least one of selection markers. For example, the expression vector can be phage, plasmid, cosmid, minichromosome, virus, or retrovirus comprising the polynucleotide.

The expression vector comprising the polynucleotide encoding the human monoclonal antibody can be the expression vector containing each polynucleotide respectively encoding the human monoclonal antibody heavy chain or light chain, or can be the expression vector comprising both polynucleotides encoding the heavy chain and light chain.

The transformant introduced with the expression vector of the invention is not limited, and can be exemplified by bacteria cells transformed by the insertion of this expression vector such as *E. coli, streptomyces*, and *Salmonella typhimurium*; yeast cells; fungal cells such as *Pichia pasteris*; insect cells such as drosophila cells and *Spodoptera frugiperda* Sf9 cells; animal cells such as CHO (Chinese hamster ovary) cells, SP2/0 (mouse myeloma) cells, human lymphoblastoid cells, COS cells, NSO (mouse myeloma) cells, 293T cells, bow melanoma cells, HT-1080 cells, BHK (baby hamster kidney) cells, HEK (human embryonic kidney) cells, and PERC.6 (human retinal cells); and plant cells.

In this invention, the term "introduction" indicates the method to deliver the vector containing the polynucleotide encoding the monoclonal antibody into a host cell. Such introduction can be performed by various methods well known to those in the art, which are exemplified by calcium phosphate-DNA co-precipitation, DEAE-dextran-mediated transfection, polybrene-mediated transformation, electroporation, microinjection, liposome fusion, lipofectamine-mediated method, and protoplast fusion. Also, the transfection indicates the means to deliver a target material into a cell by using virus particles via infection. In addition, the vector can be introduced into a host cell by gene bombardment. In this invention, the term "introduction" can be used alike as the term "transformation".

The present invention also provides a method for eliminating the undifferentiated human pluripotent stem cells containing the step of reacting human pluripotent stem cells with an agent that is specifically binding to Desmoglein 2 protein. Particularly, the agent that specifically binds to Desmoglein 2 protein is as described hereinbefore, and the step of eliminating is to eliminate the pluripotent stem cells that remain undifferentiated in the differentiated cells finished with the differentiation from pluripotent stem cells by using the antibody, which can be achieved by the conventional method well informed to those in the art. So, the method of the invention is effective in eliminating the undifferentiated human pluripotent stem cells.

The analysis of the difference among the undifferentiated human embryonic stem cells, mouse embryonic stem cells, and mouse feeder cells is possibly made by using the monoclonal antibody of the present invention. So, the monoclonal antibody of the invention can be effectively used for the separation of human embryonic stem cells.

It has not been completely confirmed yet that Desmoglein 2 protein is expressed in the surface of the undifferentiated human pluripotent stem cells. So, the present inventors first separated the undifferentiated human pluripotent stem cells with high purity by using the corresponding antibody. In particular, the present invention provides a method for detecting, identifying, and separating the undifferentiated human pluripotent stem cells by using the monoclonal antibody 6-1 constructed in this invention. The present invention thus provides the functional cells which are fully differentiated and have no undifferentiated human pluripotent stem cells remaining therein by using the antibody of the invention in order to use these functional cells efficiently for cell therapy.

Particularly in this invention, the undifferentiated human pluripotent stem cells can be selectively detected, separated, and eliminated via antigen-antibody complex reaction by using the Desmoglein 2 specific antibody or the antibody fragment containing its antigen binding site.

Herein, the term "antigen-antibody complex reaction" can be accomplished by immunohisto staining, radio-immuno assay (RIA), enzyme-linked immunosorbent assay (ELISA), Western blotting), immunoprecipitation assay, immunodiffusion assay, complement fixation assay, flowcytometry, and protein chip assay, but not always limited thereto.

ADVANTAGEOUS EFFECT

The monoclonal antibody of the present invention binds to Desmoglein 2 expressed in the undifferentiated human pluripotent stem cells, so that it can be used not only for the identification and separation of the undifferentiated human pluripotent stem cells but also for eliminating the undifferentiated human pluripotent stem cells from the differentiated cells in cell therapy.

BRIEF DESCRIPTION OF THE DRAWINGS

The application of the preferred embodiments of the present invention is best understood with reference to the accompanying drawings, wherein:

FIGS. 1A-1C are a set of photographs illustrating the undifferentiated status of the cultured human pluripotent stem cells.

FIG. 1A (picture 1, left side) presents the result of optical microscope observation of the cultured human pluripotent stem cells.

FIG. 1A (picture 2, right side) presents the expression of alkaline phosphatase, observed by using alkaline phosphatase (AP) staining kit.

FIG. 1B presents the result of flowcytometry of the cultured undifferentiated human pluripotent stem cells fluorescence-stained with antibodies against of SSEA1, SSEA3, and SSEA4.

FIG. 1C presents the expressions of Nanog, Oct4, and Sox2 genes in the cultured human pluripotent stem cells.

FIG. 2A is a graph illustrating the binding of the antibody 6-1 on the human embryonic stem cells H1 and H9, and induced pluripotent stem cells (iPSC), confirmed by fluorescence staining (The blue line indicates the result of using the antibody 6-1 and the red background indicates the case of using the secondary antibody alone.).

FIG. 2B illustrates that the monoclonal antibody 6-1 did not bind to the mouse embryonic stem cell line J1 or the mouse embryonic fibroblast cell line MEF. Anti-SSEA1 is the antibody that does not bind to human pluripotent stem cells but bind to mouse embryonic stem cells.

FIG. 2C illustrates that the antibody 6-1 binding site is the same as each antibody against the human pluripotent stem cell markers EpiCAm, TRA-1-60, and TRA-1-81 binding site on the surface of the human pluripotent stem cell line H9.

FIG. 4A illustrates that the peptide fragment obtained from the immunoprecipitated protein which was separated on 10% SDS-PAGE and cut off using trypsin was 37% homologous with human Dsg2, confirmed by Q-TOP.

FIG. 4B illustrates the overlapping area between the fragment (red letter) and Dsg2 amino acid sequence (black letter), suggesting that the antigen which the antibody 6-1 can recognize is Dsg2 (Desmoglein 2).

FIG. 7 presents the nucleotide sequence and the amino acid sequence of the heavy chain variable region ($V_H$) of the monoclonal antibody 6-1 along with CDR (Complementarity Determining Region) and the sites of the major amino acid residues binding to antigen. CDR is presented as bold.

FIG. 8 presents the nucleotide sequence and the amino acid sequence of the light chain variable region ($V_L$) of the monoclonal antibody 6-1 along with CDR (Complementarity Determining Region) and the sites of the major amino acid residues binding to antigen. CDR is presented as bold.

FIG. 12A presents that the expression of Dsg2 was reduced when Dsg2 was knocked-down with shRNA, confirmed by real-time PCR and Western blotting.

FIG. 12B illustrates the shape and AP positive response in the Dsg2 knocked-down human pluripotent stem cells in the undifferentiation culture condition.

FIG. 12C illustrates the decrease of the expressions of some of the transcription factors necessary for maintaining undifferentiation condition and the increase of the expressions of the endoderm, mesoderm, and ectoderm marker genes in the Dsg2 knocked-down human pluripotent stem cells.

FIG. 12D presents that the expressions of the undifferentiation markers Oct4, Sox2, Nanog, and c-Myc were reduced in the Dsg2 knocked-down human pluripotent stem cells and the expression of the cell cycle positive regulator Cyclin D1 was reduced but the expression of the cell cycle negative regulator p21 was increased in the Dsg2 knocked-down human pluripotent stem cells, confirmed by Western blotting.

DESCRIPTION OF THE PREFERRED EMBODIMENTS

Figures 2A, 2B:
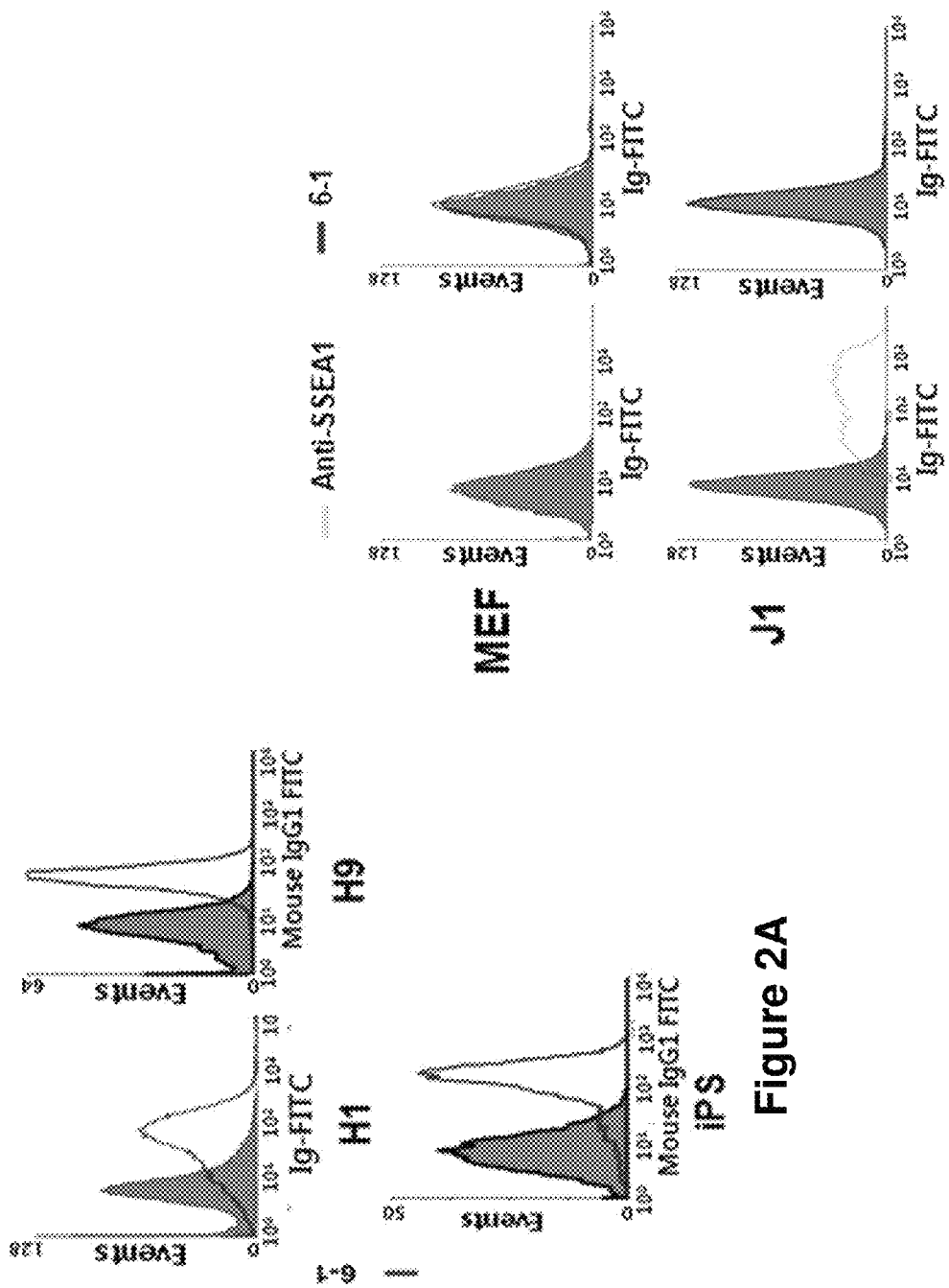
FIGS. 2A-2C illustrate the binding of the monoclonal antibody 6-1 onto the surface of human pluripotent stem cells.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Human Pluripotent Stem Cell Culture and Confirmation of the Undifferentiation Status Thereof <1-1> Culture of Human Pluripotent Stem Cells To construct a novel monoclonal antibody that can recognize human embryonic stem cells specifically, the human embryonic stem cell lines H1 and H9, and the induced pluripotent stem cell (iPSC) line were distributed from National Institute of Health (NIH, USA) and ATCC. The cells were cultured in DMEM (Dulbecco's modified Eagle's medium)/F12 (Gibco, Rockville, Md., USA) supplemented with 20% Knockout SR (Gibco), 0.1 mM β-mercaptoethanol (Sigma, St Luis, Mo., USA), 2 mM glutamine (Gibco), 0.1 mM non-essential amino acid (Gibco), 100 U/ml penicillin G (Sigma), 100 μg/ml streptomycin (Sigma), and 5 ng/ml bFGF (Gibco Invitrogen), followed by sub-culture every 5~7 days.

Particularly, a tissue culture plate (Nunc) was coated with 0.1% gelatin solution at 37° C. for 30 minutes. MEF (mouse embryonic fibroblast, Korea Research Institute of Bioscience and Biotechnology) irradiated with gamma-ray at 3000 rad was inoculated therein at the density of $1.6 \times 10^4/cm^2$. The irradiated MEF was the cell that did not grow but supported the growth of human embryonic stem cells. The human embryonic stem cell tissue that had been culture for 5~7 days was treated with 1 mg/ml of collagenase IV (Gibco) at 37° C. for 1 hour, and then the stem cell tissue was cut in an appropriate size. The prepared sections were loaded in the MEF tissue culture plate. The culture medium was replaced from 48 hours every day in the course of culture.

<1-2> Confirmation of the Undifferentiation Status of the Cultured Human Pluripotent Stem Cells To investigate whether or not the human pluripotent stem cells cultured for 6~7 days by the method described in Example <1-1> could remain as undifferentiated, the cells were stained by using alkaline phosphatase (AP) staining kit (Sigma). As a result, it was confirmed that AP was expressed in the cells, suggesting that the cells were still as undifferentiated (FIG. 1A-2).

The cultured cells were fluorescence-stained with SSEA (stage specific embryonic antigen), followed by flow cytometry. As a result, it was confirmed that the cells were negative to SSEA1 that was not the undifferentiation marker but were positive to SSEA3 and SSEA4 which were the undifferentiation markers, suggesting that the cells were still as undifferentiated (FIG. 1B). To investigate whether or not Oct 4 gene that was not expressed in mouse embryonic stem cells would be expressed in human pluripotent stem cells, RT-PCR was performed with Nanog, Oct4, and Sox2 specific primers. Also, RT-PCR for RNA quantification was performed with hGAPDH and mActin primers. The sequences of those primers are presented in Table 1.

TABLE 1

| Primer name | | Sequence | SEQ. ID. NO: |
|---|---|---|---|
| Nanog | Forward | TGCCTCACACGGAGACTGTC | 1 |
| | Reverse | TGCTATTCTTCGGCCAGTTG | 2 |
| Oct4 | Forward | CGACCATCTGCCGCTTTGAG | 3 |
| | Reverse | CCCCCTGTCCCCCATTCCTA | 4 |
| Sox2 | Forward | TACCTCTTCCTCCCACTCCA | 5 |
| | Reverse | ACTCTCCTCTTTTGCACCCC | 6 |
| Dsg2 | Forward | AGGTATGGCCAAGGAAGCCACGA | 7 |
| | Reverse | ATAGCGCCTGTGGCCCCTGTAA | 8 |
| Pax6 | Forward | AACAGACACAGCCCTCACAAACA | 9 |
| | Reverse | CGGGAACTTGAACTGGAACTGAC | 10 |
| CD34 | Forward | TGAAGCCTAGCCTGTCACCT | 11 |
| | Reverse | CGCACAGCTGGAGGTCTTAT | 12 |
| AFP | Forward | CCATGTACATGAGCACTGTTG | 13 |
| | Reverse | CTCCAATAACTCCTGGTATCC | 14 |
| hGAPDH | Forward | ACCACAGTCCATGCCATCAC | 15 |
| | Reverse | TCCACCACCCTGTTGCTGTA | 16 |
| mActin | Forward | AGGCCCAGAGCAAGAGAGG | 17 |
| | Reverse | TACATGGCTGGGGTGTTGAA | 18 |

After the PCR, the PCR product was electrophoresed on 1.5% agarose gel and as a result, the expressions of Oct4, Nanog, and Sox 2 genes were confirmed, suggesting that the cells still remained as undifferentiated (FIG. 1C). In FIG. 1, MEF indicates mouse embryonic stem cells, and H9, H1, and iPSC are human pluripotent stem cells.

Then hybridoma was constructed by immunizing mouse with the undifferentiated human pluripotent stem cells.

Example 2: Construction of Mouse Hybridoma

The human pluripotent stem cells (H9) cultured by the method described in Example <1-1> was separated by treating with collagenase IV. Approximately $2 \times 10^6$ cells were suspended in 100 μl of PBS, which were then irradiated with γ-ray to inactivate the stem cells. The cells were then intraperitoneally injected in Balb/c mouse. The injection was repeated three times every three weeks and lastly performed 3 days before cell fusion.

To collect feeder cells, 20 ml of DMEM (GIBCO) was filled in the peritoneum of a health mouse one day before cell fusion. DMEM was then absorbed out from the mouse, by which peritoneal cells were collected. The collected cells proceeded to centrifugation. Also, normal spleen was pulverized, from which cells were extracted. These two types of cells were mixed, to which 20% FBS was added. The mixed cells were distributed in a 96-well plate at the density of $10^5$ cells/well, followed by culture in a 37° C. $CO_2$ incubator. NS1 myeloma cell line (TIB-18™, ATCC, USA) which would be fused with spleen cells two weeks after were cultured in RPMI1640 (GIBCO) supplemented with 10% FBS for 2 weeks before cell fusion.

The spleen was extracted from the mouse immunized with the human pluripotent stem cells and then washed well with RPMI1640 (GIBCO). The spleen was pulverized on Petri dish by using a glass rod and the cell suspension was left in a 15 ml tube for a while. When debris were precipitated, the supernatant was transferred into a new tube. NS1 was obtained by centrifugation and resuspended in 10 ml of RPMI 1640. The numbers of NS1 and the spleen cells were counted. $10^7$ NS1 and $10^8$ spleen cells were mixed in a 50 ml tube, followed by centrifugation at 200×g for 5 minutes. After eliminating the supernatant, the precipitate was left in a beaker filled with water at 37° C. for 2 minutes. The tube was tapped lightly to make the cells soft and was shaken in 37° C. water, during which 1 ml of PEG solution (GIBCO) was added thereto for 1 minute. Centrifugation was performed at 100×g for 2 minutes, to which 5 ml of RPMI1640 was slowly added for 3 minutes. 5 ml of RPMI1640 was slowly added thereto again for 2 minutes, followed by centrifugation at 200×g to recover the cells. The collected cells were resuspended carefully in 30 ml of normal medium (RPMI1640+20% FBS). The cells were left in a 37° C. $CO_2$ incubator for 30 minutes and then distributed in a 96-well plate where MEF cells (feeder cells that had been cultured in advance) were layered, at the density of $10^5$ cells/well (70 μl per well), followed by culture in a 37° C. $CO_2$ incubator. On the next day, 70 μl of HAT was added to each well of the plate. The cells were cultured in HAT medium at least for 2 weeks, during which colony formation was observed every three days.

To select the clone expressing the antibody, sandwich ELISA (Enzyme Linked Immunosorbent Assay) was performed. 100 μl of the hybridoma culture medium was added to the plate coated with 2 μg/ml of IgG or IgM antibody, followed by reaction at 37° C. for 1 hour. Again, the cells were added with HRP (horseradish peroxidase, Sigma) conjugated anti-mouse IgG or IgM (1/5,000), followed by reaction for 1 hour. The plate was washed with phosphate buffer containing 0.05% tween 20, to which substrate solution containing OPD (Sigma) and $H_2O_2$ was added. Then, $OD_{492}$ was measured, leading to the selection of the clones producing the antibody.

Example 3: Separation of the Monoclonal Antibody Binding to Human Pluripotent Stem Cells <3-1> Selection of the Hybridoma Clone Producing the Monoclonal Antibody which Binds to Human Pluripotent Stem Cells Among those clones prepared in Example 2, the hybridoma clone which secreted the antibody comparatively stably was selected and the binding capacity to human pluripotent stem cells was investigated. Particularly, the cultured human pluripotent stem cells were separated by using collagenase IV. The cells were treated with cell separation buffer (GIBCO) for 20 minutes at 37° C., leading to the separation of the cells as single cells. The cells were passed through 40 μm strainer, and $2 \times 10^5$ cells proceeded to flow cytometry. The human pluripotent stem cells prepared as single cells were suspended in PBA (1% BSA was dissolved in PBS), followed by reaction with the antibody supernatant at 4° C. for 30 minutes. Centrifugation was performed at 4° C. at 1200 rpm for 5 minutes and 100 μl of the supernatant was eliminated. The anti-mouse Ig-FITC (BD) was diluted (1:200). The cells were reacted with the diluted anti-mouse Ig-FITC at 4° C. for 30 minutes, and then washed with PBA twice. Propidium iodide (PI) negative cells were selected for the investigation of binding capacity of the cells to human pluripotent stem cells by using FACS caliber.

As a result, various hybridomas secreting the antibody binding to human pluripotent stem cells were selected and sub-cultured, during which subcloning was performed as well. At last, the hybridoma that secreted the antibody 6-1 and had kept the specificity to human pluripotent stem cells with maintaining the stability was selected.

The selected hybridoma secreting the antibody 6-1 was named 'hybridoma 6-1'

<3-2> Purification of Monoclonal Antibody

The antibody 6-1 was purified from the hybridoma 6-1 selected in Example <3-1>.

Particularly, in order to purify the antibody 6-1, $1 \times 10^7$ hybridoma cells dissolved in 0.5 ml of PBS was intraperitoneally injected in Balb/c mouse inoculated with 0.5 ml of pristane a week earlier. 10~14 days after the injection, ascites was extracted by using a syringe. The ascites proceeded to centrifugation and the supernatant was collected. 1 ml of PBS was added to 1 ml of the extracted ascites to dilute, resulting in 2 ml of ascites. 1 nM EDTA and 0.02% NaN$_3$ were added to the ascites, which was then filtered with 0.22 μm filter. The antibody conjugation was induced by using protein G-sepharose column at 4° C. for 2 hours while rotating the solution. Then, the column was raised straight and the wall of the column was washed with washing buffer (0.5 M NaCl, 0.1 M Tris, pH 8.0) by using a serum separator. The column was connected with a peristatic pump to wash the column fully. After washing the column, the antibody was eluted by using 0.2 M glycin-HCL (pH 2.7). The eluent was buffered in a tube containing 1 M Tris (pH 9.0). Then, dialysis was performed in PBS (pH 7.4) 4 times, and the resultant antibody was stored at −20° C.

Example 4: Binding Capacity of the Antibody 6.1 to Undifferentiated Human Pluripotent Stem Cells To investigate the binding capacity of the antibody 6-1 purified in Example <3-2> to human pluripotent stem cells, fluorescence staining was performed by the same manner as described in Example <3-1> (FIG. 2A). Three kinds of pluripotent stem cells (H1, H9, and iPSC) were used herein. The red background indicates the case of using the secondary antibody alone. SSEA1 is the antibody that did not bind to human pluripotent stem cells, and SSEA3 and SSEA4 are the antibodies that bind to human pluripotent stem cells which are the undifferentiation makers. In FIG. 2A, the blue line illustrates the fluorescence staining of human pluripotent stem cells with the monoclonal antibody 6-1, wherein the antibody 6-1 bound to all of those three kinds of human pluripotent stem cells.

Mouse embryonic stem cells (J1) (Li. et al., Cell, 69:906-915, 1992) and mouse embryonic fibroblasts (MEF) were cultured in DMEM (GIBCO) supplemented with 10% FBS, followed by separation with collagenase IV. To investigate the binding capacity of the antibody 6-1 to the mouse embryonic stem cells (J1) and the mouse embryonic fibroblasts (MEF) by the same manner as described in the above, flow cytometry was performed along with fluorescence staining. As a result, it was confirmed that the antibody 6-1 did not bind to J1 or MEF (FIG. 2b).

Figure 2C:
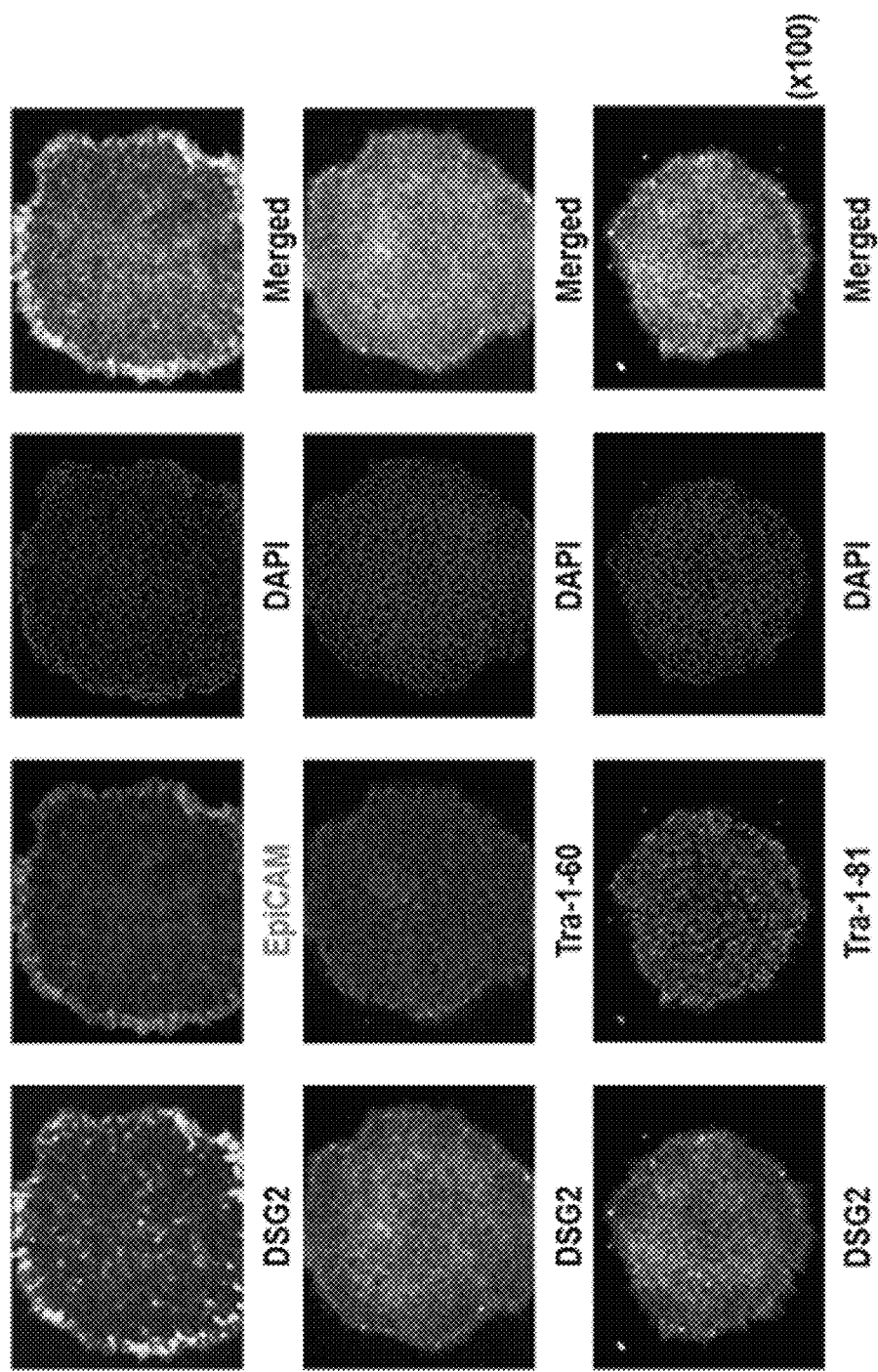

When the antibodies against the undifferentiated human pluripotent stem cell surface markers EpiCAM, Tra-1-60, and Tra-1-81 were added to H9, the embryonic stem cells, together with the antibody 6-1 and when fluorescence staining was performed with that, each of the antibody was co-localized with the antibody 6-1 on the cell surface (FIG. 2C). From the above results, as shown in FIG. 2, it was confirmed that the antibody 6-1 bound to the undifferentiated human embryonic stem cells.

Example 5: Separation and Identification of the Antigen Binding to the Antibody 6-1

Figure 3:
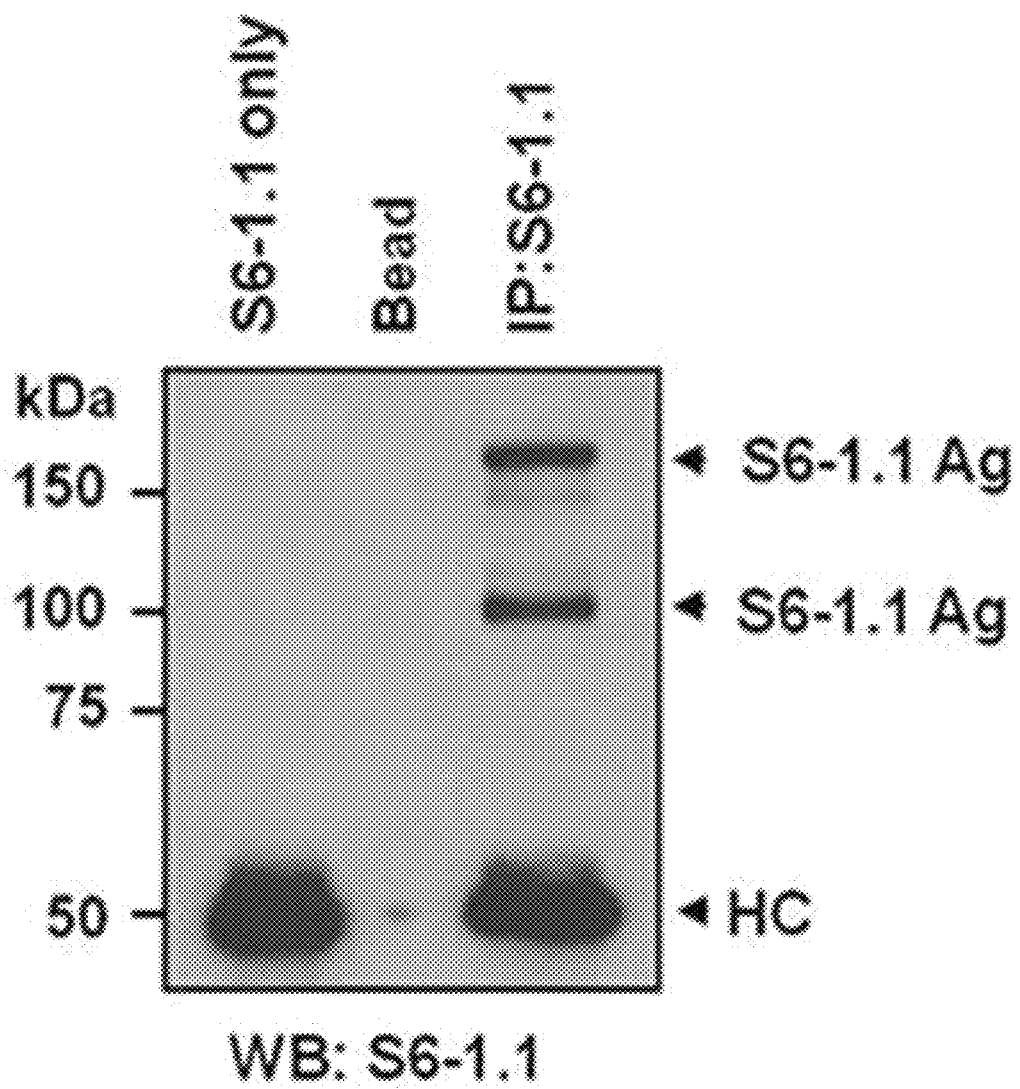
FIG. 3 presents the result of immunoprecipitation with the molecule binding to the antibody 6-1, wherein the surface of human pluripotent stem cell line H9 was biotinylated and the protein precipitated by immunoprecipitation using the antibody 6-1 was detected by Western blotting.

<5-1> Separation of the Antigen Binding to the Antibody 6-1 by Immunoprecipitation To separate the human pluripotent stem cell surface marker that can be recognized by the monoclonal antibody 6-1, the cultured human pluripotent stem cells (H9) were washed with PBS, followed by biotinylation with EZ-Link Sulfo-NHS-LC-Biotin (Pierce, Rockford, Ill.). The cells were lysed in lysis buffer (25 mM Tris-HCl, pH 7.5, 250 mM NaCl, 5 mM EDTA, 1% Nonidet P-40, 2 g/ml aprotinin, 100 g/ml phenylmethylsulfonyl fluoride, 5 g/ml leupeptin) at 4° C. for 20 minutes, and the nuclei were eliminated by centrifugation. The protein concentration was determined by using BCA (bicinchoninic acid) protein assay kit (Pierce). The protein non-specifically binding to protein G plus-sepharose was reacted with 20 μl of protein G plus-sepharose at 4° C. for 2 hours, followed by centrifugation to obtained the supernatant. The obtained supernatant was reacted with approximately 1 mg of the antibody at 4° C. for 12 hours, to which 20 μl of protein G plus-sepharose was added again, followed by reaction at 4° C. for 2 hours. Then, centrifugation was performed and the precipitate was recovered. The recovered precipitate was washed with the cell lysate at least 10 times, and the remaining protein was separated by 10% SDS-PAGE. The protein proceeded to Western blotting on nitrocellulose membrane. The nitrocellulose membrane was reacted in PBST (PBS+0.1% Tween 20) containing 5% skim milk for 1 hour and then washed with PBST at least twice, followed by reaction with streptavidin-HRP (horseradish peroxidase) conjugate (1:1,500, Amersham Biosciences) for 1 hour. After washing the membrane with PBST 5 times, the color development was induced with ECL detection reagent (Amersham Biosciences). As a result, it was confirmed that the monoclonal antibody 6-1 bound to the protein having the molecular weight of 165 kDa or 100 kDa (FIG. 3).

<5-2> Separation and Identification of the Antigen Binding to the Antibody 6-1

Figure 4A:
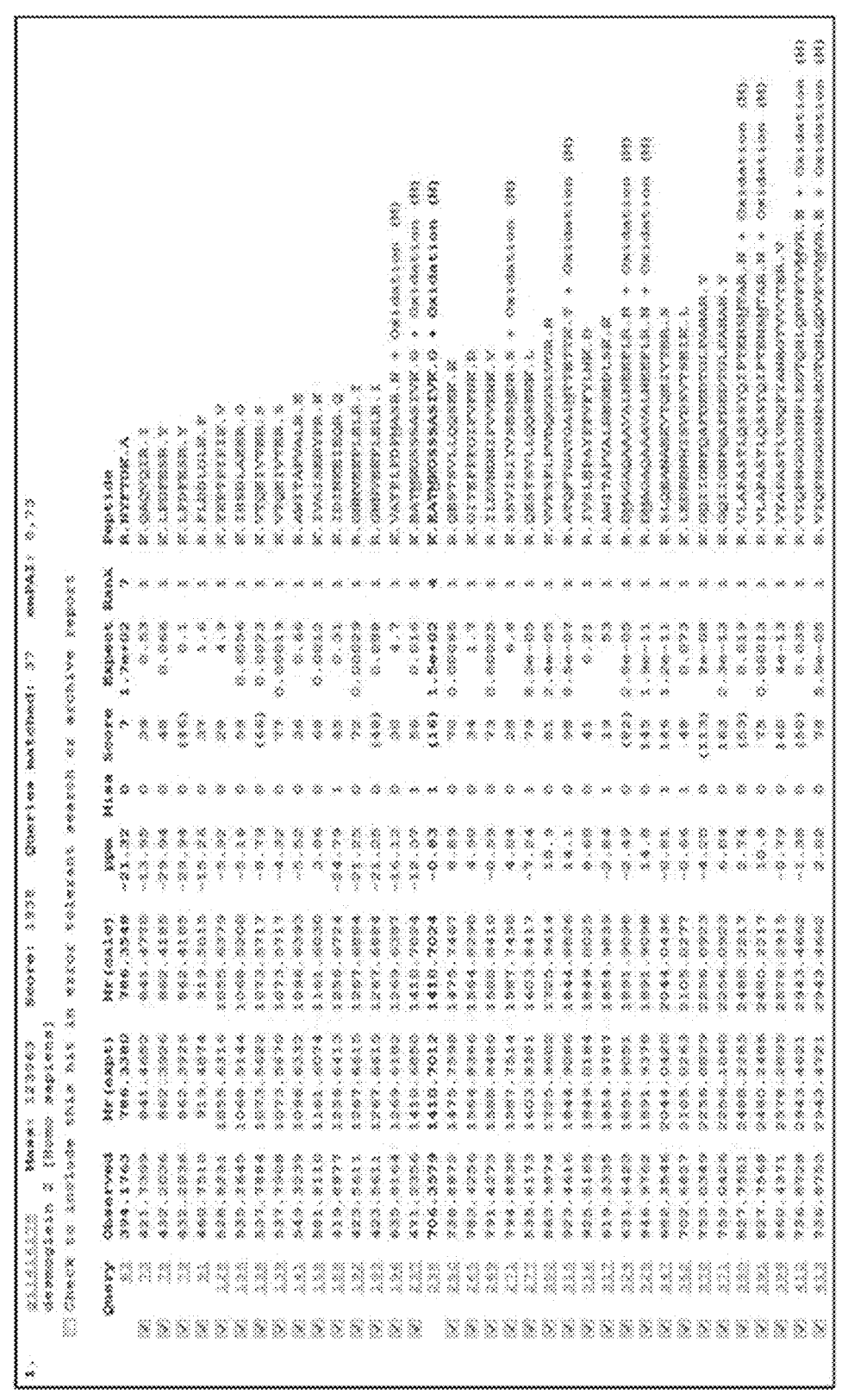

To collect the protein conjugated with the antibody 6-1, the cell lysate obtained from $1 \times 10^8$ H9 cells proceeded to immunoprecipitation by the same manner as described in Example <5-1>. 10% SDS-PAGE was performed and the gel was stained with Coomassie G250 (BIO-RAD). The SDS gel harboring the protein immunoprecipitated by the monoclonal antibody 6-1 was stained with Coomassie G250 (BIO-RAD) according to the manufacturer's protocol. The region that contained the protein was cut out and washed with 30% methanol for 5 minutes, which was then shattered. The gel fragments were reacted in 30% methanol until the stained color was completely gone. The gel fragments were dehydrated with 100% acetonitrile for 10 minutes, and then completely dried in a vacuum centrifuge for 30 minutes. The gel fragments were added with 300 ng trypsin (Promega) and 50 mM ammonium bicarbonate solution, followed by reaction at 37° C. for 16 hours to cut the protein out. The peptide cut out therefrom was extracted with 100 μl of 50 mM ammonium bicarbonate three times, which was then dried in a vacuum centrifuge. The peptide mixture was analyzed by ESI Q-TOF MS/MS (electrospray quadrupole time of flight tandem mass spectrometry) in Q-TOF micro (MicroMass). As a result, the protein recognized by the antibody 6-1 was identified as Desmoglein 2 (FIG. 4). In FIG. 4, the region marked by red color indicates the amino acid sequence identified by Q-TOF.

Figure 5:
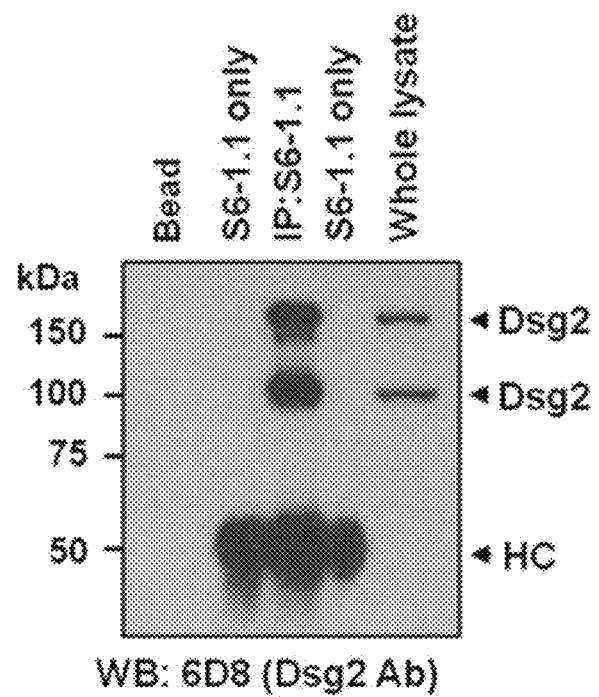
FIG. 5 illustrates that the antibody 6-1 binds to Dsg2, confirmed by Western blotting. H9 cell extract proceeded to immunoprecipitation with the antibody 6-1, and then the precipitate was separated on 10% SDS-PAGE, followed by Western blotting using the informed 6D8 antibody and streptavidin-HRP.

To confirm whether or not the antibody 6-1 would bind to Dsg2 identified above, immunoprecipitation was performed with the H9 cell extract by using the antibody 6-1. The obtained precipitate proceeded to 10% SDS-PAGE, followed by Western blotting. The immunoprecipitated protein was detected by ESL by using the monoclonal antibody 6D8 (Hycult Biotechnology) well known as the antibody against Dsg2 as the primary antibody and also using Streptavidin-HRP. As a result, it was confirmed that the Dsg2 protein immunoprecipitated by the antibody 6D8 was conjugated to the antibody 6-1 (FIG. 5). This result indicates that the target antigen of the antibody 6-1 was Dsg2.

Example 6: Analysis of the Nucleic Acid and Amino Acid Sequence of the Monoclonal Antibody 6-1

<6-1> Cloning of the Monoclonal Antibody 6-1 Gene $1 \times 10^8$ of actively growing hybridoma 6-1 cells were collected by centrifugation, which were then washed with cold PBS. 1 ml of TRIzol (Ambion, USA) was added thereto, and the mixture was well-mixed by shaking. The mixture was reacted at room temperature for 5 minutes, to which 200 μl of chloroform was added. After shaking the mixture enough, centrifugation was performed at 4° C. at 12,000×g, for 10 minutes to obtain supernatant. Isopropanol was added thereto at the same volume to the obtained supernatant, followed by mixing for 15 seconds. The mixture stood at room temperature for 10 minutes, followed by centrifugation at 12,000×g for 10 minutes to precipitate RNA. Then, the supernatant was eliminated and the pellet was left.

1 ml of 75% ethanol was added thereto. The mixture was stirred enough to let the pellet fall off from the tube and RNA was washed and the RNA pellet was collected by centrifugation performed at 4° C. at 12,000×g for 5 minutes. The remaining solvent was eliminated by using a 200 μl tip, and the RNA precipitate was dried in the air. An appropriate amount of nuclease-free water was added thereto, followed by culture in a 56° C. heat block for 5 minutes. After the pellet was completely dissolved, RNA was quantified by measuring A260 with spectrometer.

To synthesize the complementary DNA template, 2 μg of total RNA was conjugated with dNTP oligo primer via reaction at 65° C. for 5 minutes in a thermal cycler (TAKARA, Japan) by using First-Strand cDNA Synthesis kit (Invitrogen, USA). As a result, the oligo primer conjugated RNA template was obtained, to which a necessary cofactor such as reverse transcriptase and $MgCl_2$ was added. Then, DNA template was synthesized at 50° C. for 50 minutes.

For cloning of the DNA template, the well known PCR primer was used with modification (Wang, et al J. Immunol. Methods 233, 167-177, 2000).

For cloning of heavy chain, 10 pmole of each oligonucleotide [IgG1 constant region PCR primer 5'-ATA GAC AGA TGG GGG TGT CGT TTT GGC-3' (SEQ. ID. NO: 51), heavy chain variable region N-terminal primers 5'MH1 5'-SAR GTN MAG CTG SAG SAG TC-3' (SEQ. ID. NO: 52) and 5'MH2 5'-SAR GTN MAG CTG SAG SAG TCW GG-3' (SEQ. ID. NO: 53)] was mixed with 50 μl of total reaction mixture, to which Takara Ex Taq (TAKARA, Japan) and reaction buffer were added, resulting in the preparation of reverse transcription polymerase chain reaction mixture.

For cloning of light chain, each oligonucleotide [kappa chain constant region primer 5'-GGA TAC TAC AGT TGG TGC AGC ATC-3' (SEQ. ID. NO: 54), kappa chain variable region N-terminal primers 5'MK 5'-GAY ATT GTG MTS ACM CAR WCT MCA-3' (SEQ. ID. NO: 55), 5'-GAC ATT GTG CTG ACC CAA TCT CCA GCT TCT-3' (SEQ. ID. NO: 56) and 5'-GAC ATT CAG CTG ACC CAG TCT CCA-3' (SEQ. ID. NO: 57)] was prepared likewise. Among these primers corresponding to the variable region N-terminal, S stands for G or C, R stands for A or G, N stands for A, C, G, or T, M stands for A or C, W stands for A or T, and Y stands for T or C. The reaction mixtures for heavy chain and light chain prepared above were mixed, followed by reaction at 94° C. for 1 minute, at 45° C. for 1 minute, and at 72° C. for 2 minutes (30 cycles).

Figure 6:
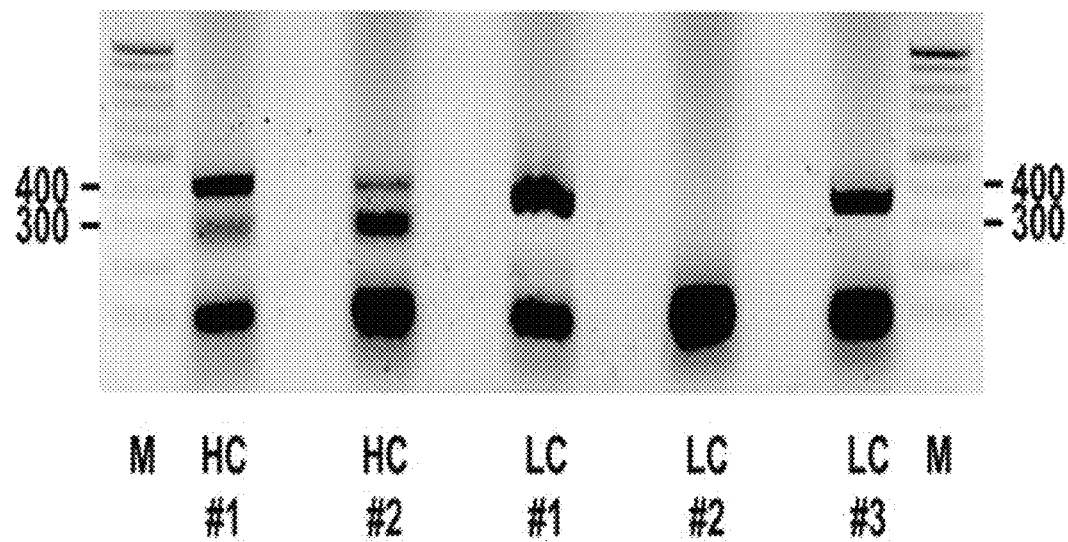
FIG. 6 presents the amplified DNA used for the sequencing of the heavy chain and the light chain variable regions of the monoclonal antibody 6-1. Herein, HC indicates the heavy chain region and LC indicates the light chain region.

As a result, a band in approximately 380 bp which was presumed to be the DNA fragment corresponding to the heavy chain constant region was observed in the site of the combination of SEQ. ID. NO: 51, NO: 52 or NO: 53 (FIG. 6, HC #1 and #2) and another band in approximately 350 bp which was presumed to be the DNA fragment corresponding to the light chain constant region was observed in the site of the combination of SEQ. ID. NO: 54, NO: 55 or NO: 57 (FIG. 6, LC #1 and #3).

<6-2> Cloning and Sequence Analysis of the Monoclonal Antibody 6-1 Gene

For cloning of the antibody 6-1 gene amplified in Example <6-1>, the PCR product was first electrophoresed on 1% agarose gel. Then, DNA fragments corresponding to 380 bp and 350 bp were separated by using PrimePrep Gel Purification Kit (GeNet Bio, Korea).

Each of the separated DNA fragment was amplified by using Ex Taq in Example <6-1> for TA cloning and the reaction product was confirmed to have adenine nucleotide bound to 3'-end for TA cloning. So, the separated fragment could be inserted in the pCR2.1-TOPO vector using TOPO cloning kit (Invitrogen, USA) without any additional treatment with another enzyme. The recombinant plasmid was transfected in *E. coli* DH5α, which was cultured in a 37° C. incubator for 14 hours. 5 colonies were selected randomly among the confirmed *E. coli* colonies, which were cultured in 5 ml of LB medium supplemented with 50 μg/ml of ampicillin overnight. The plasmid DNA was separated by using DNA miniprep kit (Intron, Korea). To investigate whether or not the clone had the corresponding DNA, the restriction enzyme site of the vector 5', 3' away from the insertion target area was cut and electrophoresed on 1% agarose gel. The recombinant plasmid containing the fragment was analyzed based on M13 reverse primer (5'-CAG GAA ACA GCT ATG AC-3', SEQ. ID. NO: 58) which was the primer for pCR2.1-TOPO vector sequencing. The sequence analysis was requested to Solgent (Korea). The nucleotide sequence of each heavy chain and light chain cDNA was converted into amino acids and the arrangement of each amino acid was analyzed by using Kabat database (Johnson G. and Wu, T. T. Nucleic Acids Res. 29: 205-206, 2001). The results are shown in FIG. 7 and FIG. 8.

The numbers over the nucleotide sequences of FIG. 7 and FIG. 8 were determined by Kabat numbering. From the result of the amino acid sequencing, it was confirmed that these immune genes had the antibody structure specific residues and arrangement (FIG. 7 and FIG. 8). Particularly, among various groups of immunoglobulins, the heavy chain of the antibody 6-1 belonged to subgroup I and the light chain belonged to subgroup I as well.

It was also confirmed that the CDR residue of heavy chain variable region that could recognize the antigen corresponded to #26~#35 of CDR1, #50~#66 of CDR2, #99~#107 of CDR 3, while the CDR residue of light chain variable region that could recognize the antigen corresponded to #24~#31 of CDR1, #49~#56 of CDR2, and #88~#96 of CDR3.

Also, disulfide bond necessary for the structure was mediated by cysteine #22 and #96 of the heavy chain variable region and cysteine #23 and #87 of the light chain variable region. Therefore, the above result confirmed that the heavy chain and light chain genes were functional.

Figure 9A:
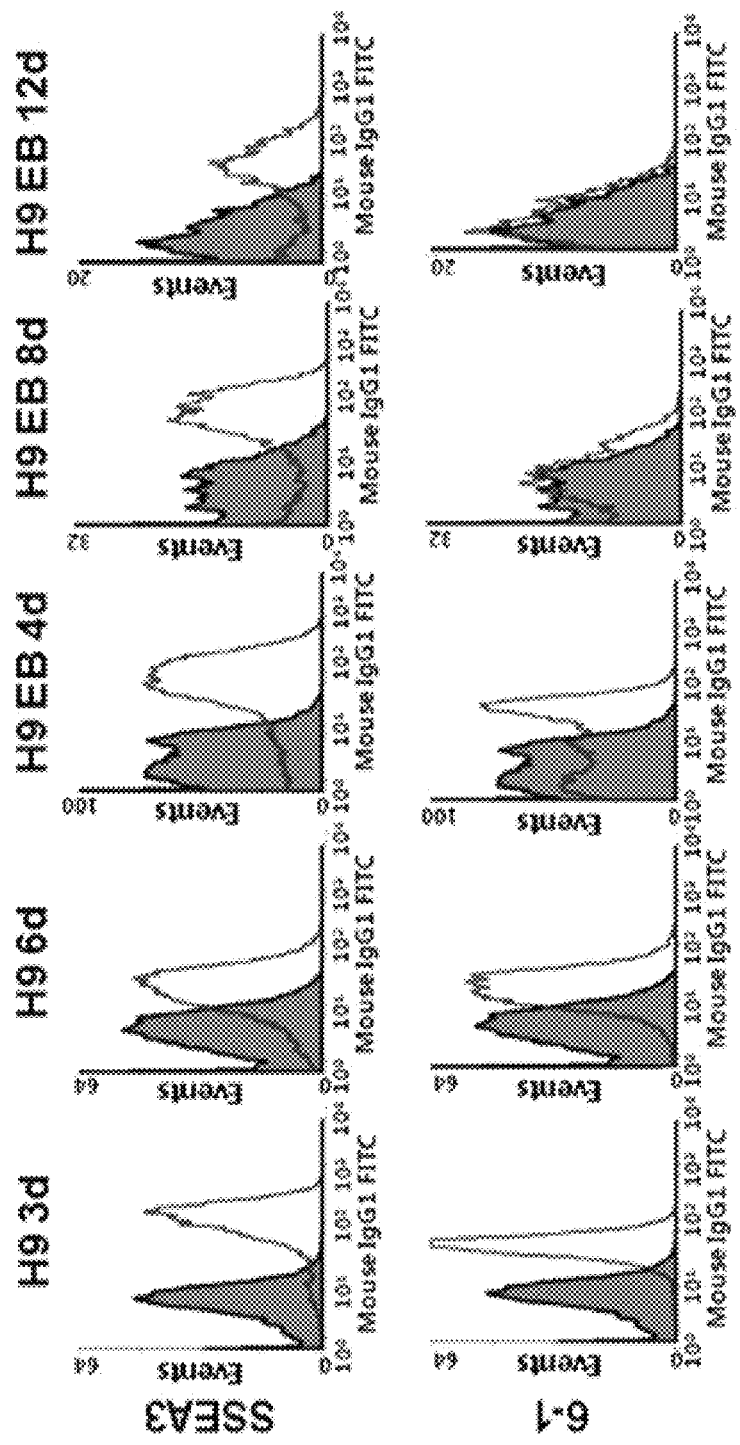
FIG. 9A presents that the binding capacities of the undifferentiation marker SSEA3 and the antibody 6-1 were decreased when human pluripotent stem cells were differentiated into embryoid body, confirmed by FACS.
Figure 9B:
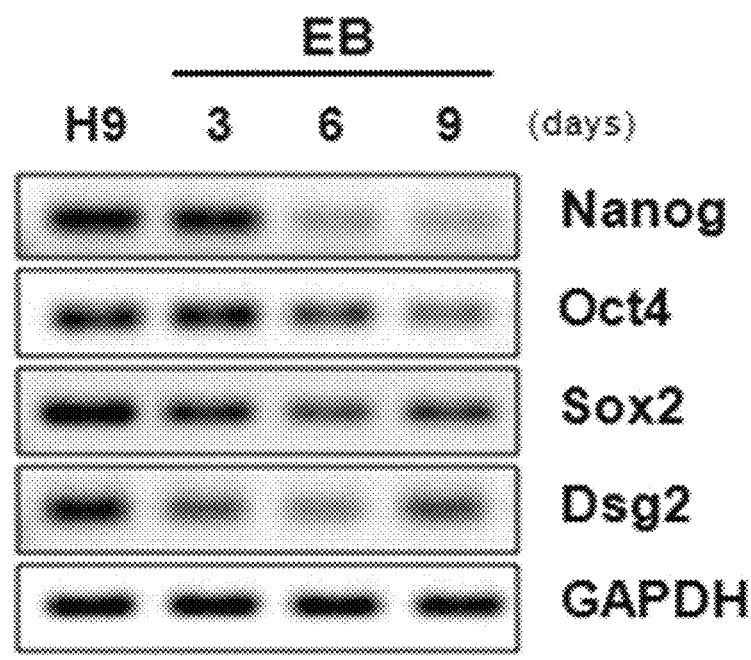
FIG. 9B presents that the expression of Dsg2 was reduced like the expressions of the undifferentiation markers Nanog, Oct4, and Sox 2 when human pluripotent stem cells were differentiated, confirmed by RT-PCR.

Example 7: Investigation of the Expression of Dsg2 on the Surface of the Undifferentiated Human Pluripotent Stem Cell Human pluripotent stem cells were separated by using collagenase as the above and the separated human pluripotent stem cell mass was carefully transferred on the bacteria plate so as not to be broken, followed by culture for 4, 8, and 12 days in EB medium [Dulbecco's modified Eagle's medium (DMEM)/F12 (Gibco) supplemented with 20% FBS (fetal bovine serum, Hyclone), 0.1 mM (β-mercaptoethanol (Sigma), 2 mM glutamine (Gibco), 0.1 mM nonessential amino acid (Gibco), 100 U/ml penicillin G (Sigma), and 100 µg/ml streptomycin (Sigma)] until embryoid body was formed. The culture medium and the plate were replaced every day. The human pluripotent stem cells differentiated by EB proceeded to FACS by the same manner as described in Example <3-1> by using the antibody 6-1. As a result, the expression of Dsg2 recognized by the antibody 6-1 was rapidly reduced just like the expression of SSEA3, the human pluripotent stem cell undifferentiation marker (FIG. 9A). The down-regulation of Dsg2 over the time was also confirmed by RT-PCR, like other undifferentiation markers Nanog, OCt4, and Sox2 (FIG. 9B).

Figure 9C:
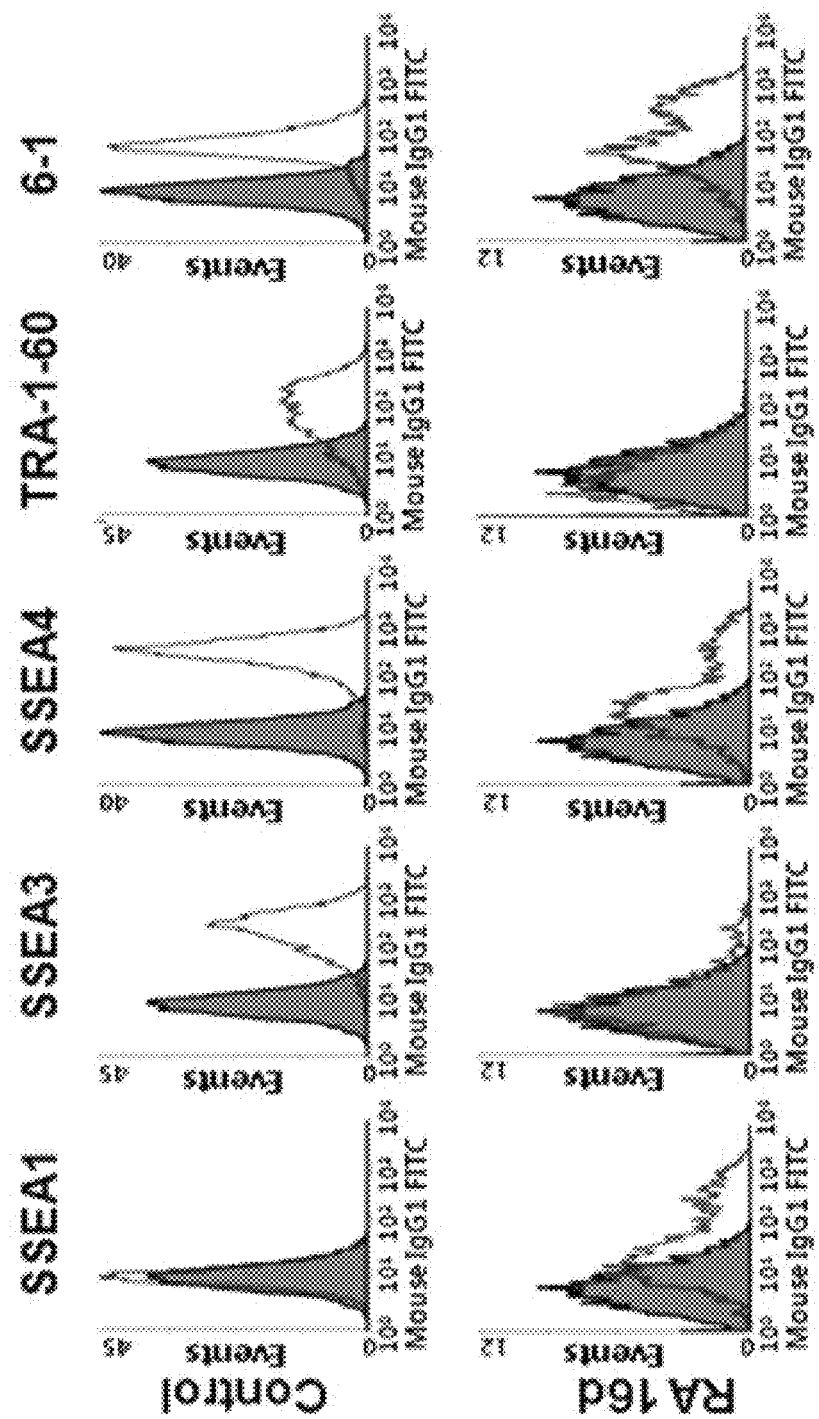
FIG. 9C presents that the binding capacity of the antibody 6-1 to embryonic stem cells was reduced in the presence of retinoic acid that could induce the differentiation of human pluripotent stem cells, confirmed by FACS.

Human pluripotent stem cells have such characteristics as being differentiated in the presence of retinoic acid, which means the stem cells lose the undifferentiation tendency when treated with retinoic acid (Henderson, et al., Stem Cells 20:329-337, 2002). So, the embryoid body cultured for 5 days was transferred onto the culture dish coated with gelatin, which was treated or not treated with $10^{-5}$M retinoic acid for 16 days. Then, the cells were collected and analyzed by FACS by the same manner as described in Example <3-1> by using the said antibody (FIG. 9C). As a result, it was confirmed that the binding capacity of the antibody 6-1 was reduced in the differentiated human pluripotent stem cells. This result indicates that Dsg2 recognized superficially by the antibody 6-1 was specifically expressed in the undifferentiated human pluripotent stem cells.

Figure 9D:
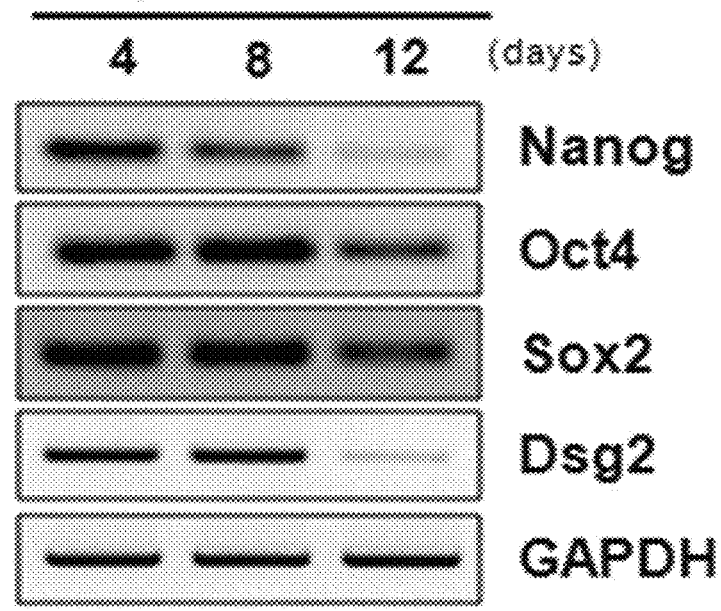
FIG. 9D presents that the expression of Dsg2 was reduced like the expressions of the undifferentiation markers Nanog, Oct4, and Sox 2 in the presence of retinoic acid, confirmed by RT-PCR.

As shown in FIG. 9D, RT-PCR confirmed that the Dsg2 expression was reduced in the cells treated with retinoic acid like the expressions of such undifferentiation markers as Nanog, Oct4, and Sox2.

Figure 10:
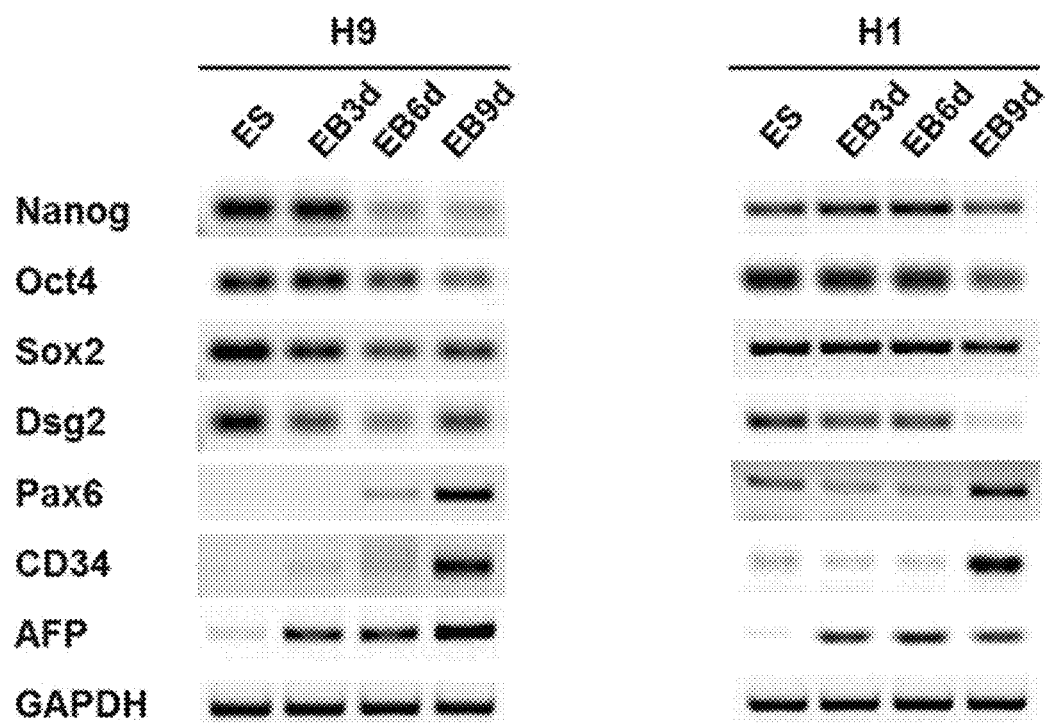
FIG. 10 presents the result of RT-PCR which investigated the expression patterns of the pluripotency related transcription factors (Nanog, Oct4, and Sox2), the 3 germ layer markers Pax6 (ectoderm), CD34 (mesoderm), and AFP (endoderm), and Dsg2 both when human pluripotent stem cells were not differentiated yet and when the cells were differentiated into embryoid body.

Further, RT-PCR was performed to investigate the expression patterns of the pluripotency related transcription factors (Nanog, Oct4, and Sox2), the three germ layer markers Pax6 (ectoderm), CD34 (mesoderm), and AFP (endoderm), and Dsg2 in the cultured undifferentiated human pluripotent stem cells and in the differentiated embryoid body. To perform RT-PCR, RNA was extracted from the embryoid body (EB; 3, 6, and 9 days) induced from H9 and H1 cells and each cell line by using TriZol reagent. 1 µg of the extracted RNA was used for the synthesis of cDNA using RT-PCR kit (SuperScript™ III first-strand synthesis system for RT-PCR, Invitrogen). The undifferentiation transcription marker primers and the differentiation marker primers listed in Table 1 were used as primers for RT-PCR. As a result, Dsg2 was expressed in the undifferentiated human pluripotent stem cells as equally as Nanog, Oct4, and Sox2, but was down-regulated in the differentiated embryoid body (EB) (FIG. 10). This result indicates that Dsg2 was the undifferentiation marker of the human pluripotent stem cells.

Example 8: Separation of the Undifferentiated Human Pluripotent Stem Cells by Using the Antibody 6-1

Figure 11A:
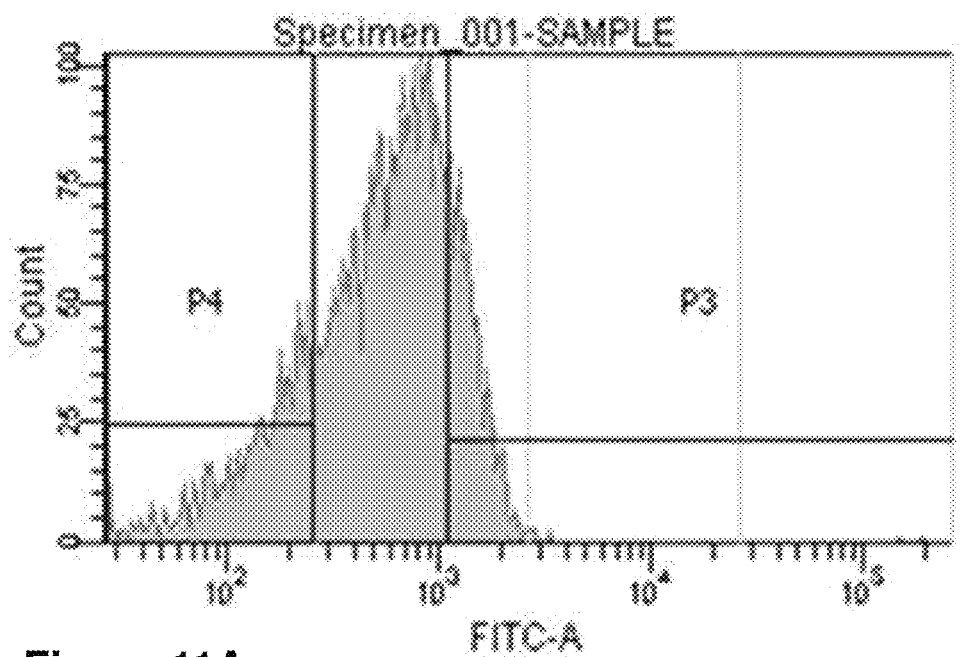
FIG. 11A presents the result of flow cytometry wherein the cultured human pluripotent stem cell line H9 was conjugated with the antibody 6-1 and then the antibody conjugated cells and the antibody non-conjugated cells were separated by flow cytometry.
Figure 11B:
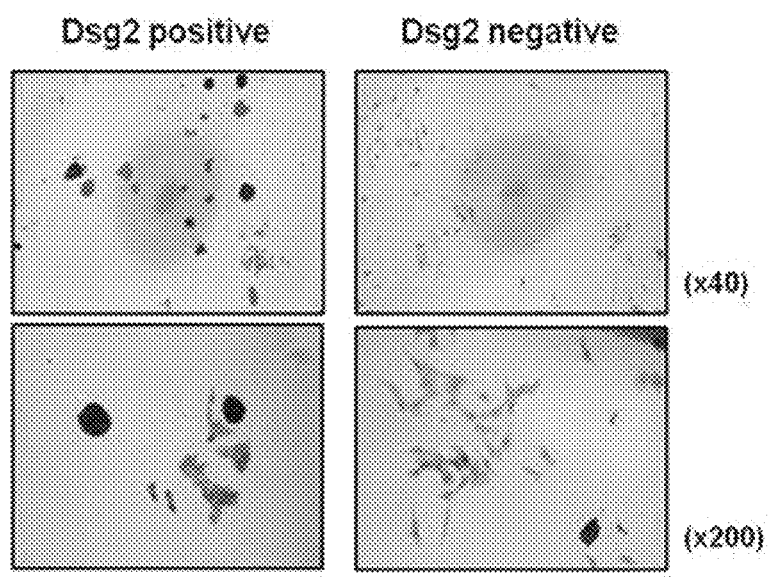
FIG. 11B illustrates that colony was formed only in the group distributed with the cell line expressing Dsg2.
Figure 11C:
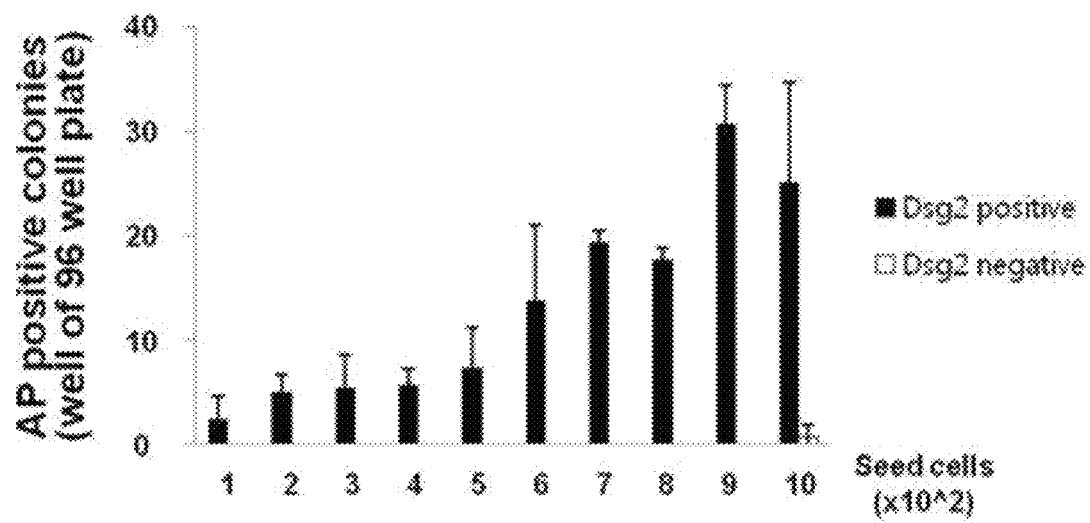
FIG. 11C illustrates that AP positive response was confirmed only in the group distributed with the cell line expressing Dsg2.

To investigate whether or not the antibody 6-1 would be useful for the separation of the undifferentiated human pluripotent stem cells, the cultured human pluripotent stem cell line H9 was conjugated with the antibody 6-1, followed by FACS using BD FACSCalibur cell sorter to separate the antibody conjugated cells (FIG. 11A, P3) and the antibody non-conjugated cells (FIG. 11A, P4). To examine the colony formation by pluripotency of the undifferentiated human pluripotent stem cells, a certain amount of cells were distributed in a 96-well plate (Falcon) coated with matrigel (BD), followed by observation. As a result, the colony formation was confirmed only in the P3 cell group expressing Dsg2 (FIG. 11B). AP staining confirmed that the AP stained colonies were formed more in the group expressing Dsg2 than in the group not expressing Dsg2 (FIG. 11C).

Figure 11D:
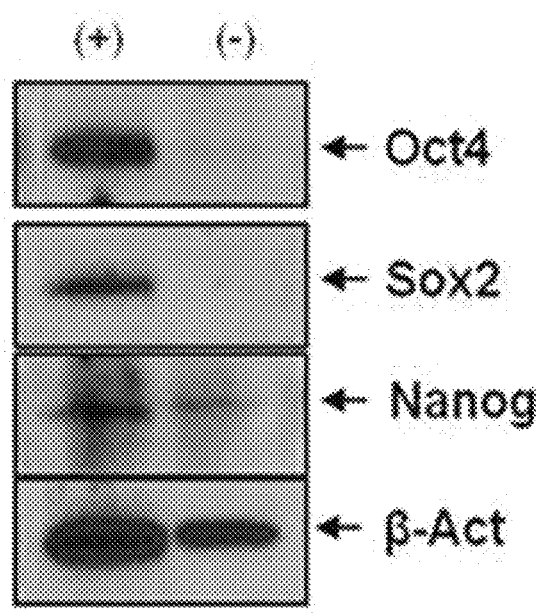
FIG. 11D presents that the expressions of the undifferentiation markers Nanog, Oct4, and Sox2 were confirmed in the cell line expressing Dsg2, confirmed by Western blotting.

To investigate the expression of the undifferentiation marker of each cell line separated according to the expression of Dsg2, the expressions of Oct4, Sox2, and Nanog were measured by Western blotting. As a result, the expressions of Oct4, Sox2, and Nanog were confirmed in the cells expressing Dsg2 (FIG. 11D). Therefore, it was confirmed that Dsg2 protein could be used as a marker for the separation of the undifferentiated human pluripotent stem cells.

Example 9: Effect of Dsg2 on Maintaining the Undifferentiation Condition of Human Pluripotent Stem Cells To investigate the effect of Dsg2 on maintaining the undifferentiation condition of human pluripotent stem cells, shDsg2 mediated lentivirus was constructed and then infected H9 cells, followed by real-time PCR and Western blotting.

Figure 12A:
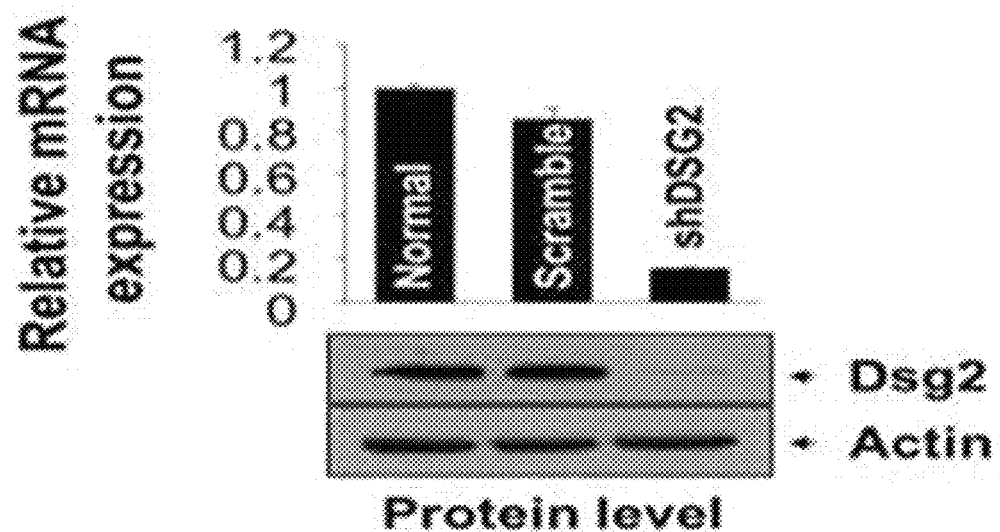
FIGS. 12A-12D present that Dsg2 was the essential factor for maintaining the undifferentiation condition of human pluripotent stem cells.
Figure 12B:
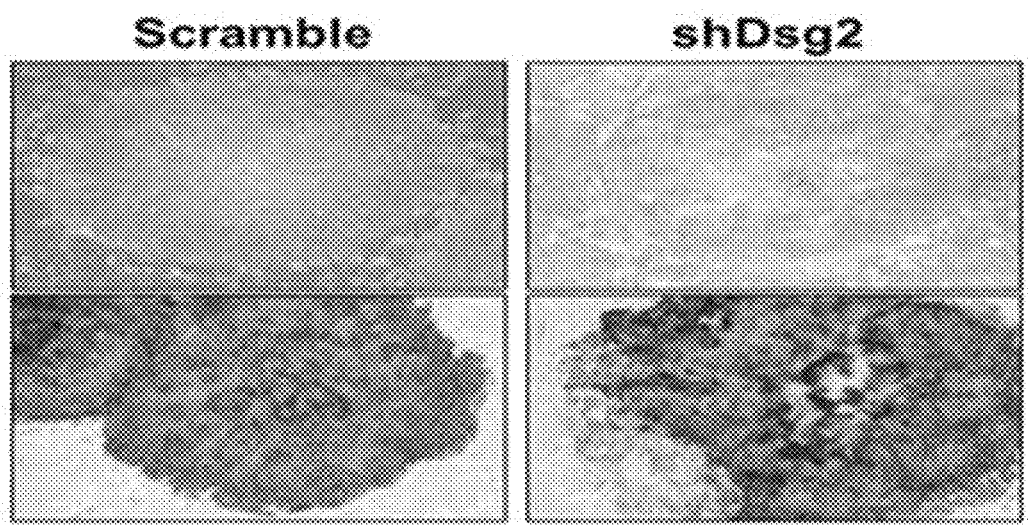

As a result, Dsg2 was down-regulated in the Dsg2 knocked-down H9 cells (shDsg2), compared with the non-treated cells and the scrambled cells having no specific target (FIG. 12A). The cell line prepared by the same manner as described in Example <1-1> was cultured in the undifferentiated human pluripotent stem cell culture condition for 5~7 days. As a result, when compared with the scrambled cells, shDsg2 cells displayed some differentiated cells in the middle of the colony, confirmed by AP staining as well (FIG. 12B).

RT-PCR was performed with the primers useful for the confirmation of the expressions of the undifferentiation markers and the three germ layer markers in mRNA obtained from three types of cells (normal, scramble, and shDsg2). The sequences of these primers used for PCR are presented in Table 2.

TABLE 2

| Primer name | | Sequence | SEQ. ID. NO: |
|---|---|---|---|
| Klf4 | Forward | TGTGATTACGCGGGCTGCGG | 19 |
| | Reverse | GGCGGTGCCCCGTGTGTTTA | 20 |

TABLE 2-continued

| Primer name | | Sequence | SEQ. ID. NO: |
|---|---|---|---|
| c-Myc | Forward | CCCAGGTCCTCGGACACCGA | 21 |
| | Reverse | TGCTCCTCTGCTTGGACGGACA | 22 |
| UTF1 | Forward | ACCAGCTGCTGACCTTGA | 23 |
| | Reverse | CTGGAGAGGGGAGACTGG | 24 |
| GDF3 | Forward | TGGTGACTCTCAACCCTGAT | 25 |
| | Reverse | ATGGTCAGTGAGAAGGGACA | 26 |
| Rex1 | Forward | CAGATCCTAAACAGCTCGCAGAAT | 27 |
| | Reverse | GCGTACGCAAATTAAAGTCCAGA | 28 |
| DNMT3B | Forward | TGCTGCTCACAGGGCCCGATACTTC | 29 |
| | Reverse | TCCTTTCGAGCTCAGTGCACCACAAAAC | 30 |
| GFAP | Forward | CCTCTCCCTGGCTCGAATG | 31 |
| | Reverse | GGAAGCGAACCTTCTCGATGTA | 32 |
| NCAM1 | Forward | ACGGAGGAGGAGAGGACCCCA | 33 |
| | Reverse | CGTTCTCCTTTGTCTGTGTGGCG | 34 |
| NEUROD1 | Forward | GCAGCGCTGGAGCCCTTCTTC | 35 |
| | Reverse | GATCCGTGGCTTTGGGCCC | 36 |
| HAND1 | Forward | TCCCTTTTCCGCTTGCTCTC | 37 |
| | Reverse | CATCGCCTACCTGATGGACG | 38 |
| IGF2 | Forward | CCCCAGATACCCCGTGGGCA | 39 |
| | Reverse | GGCGGGGTCTTGGGTGGGTA | 40 |
| COL2A1 | Forward | GGAGATCCGGGCAGAGGGCA | 41 |
| | Reverse | CCGAATTCCTGCTCGGGCCC | 42 |
| VIM | Forward | GAGAACTTTGCCGTTGAAGC | 43 |
| | Reverse | TCCAGCAGCTTCCTGTAGGT | 44 |
| LEF1 | Forward | CGGACACGAGGTGGCCAGAC | 45 |
| | Reverse | ACCGCATGGGATGGCTGCAC | 46 |

TABLE 2-continued

| Primer name | | Sequence | SEQ. ID. NO: |
|---|---|---|---|
| INS | Forward | AAGCGTGGCATTGTGGAAC | 47 |
| | Reverse | GGCTTTATTCCATCTCTCTCGG | 48 |
| HGF | Forward | GCATCAAATGTCAGCCCTGG | 49 |
| | Reverse | CAACGCTGACATGGAATTCC | 50 |

Figure 12C:
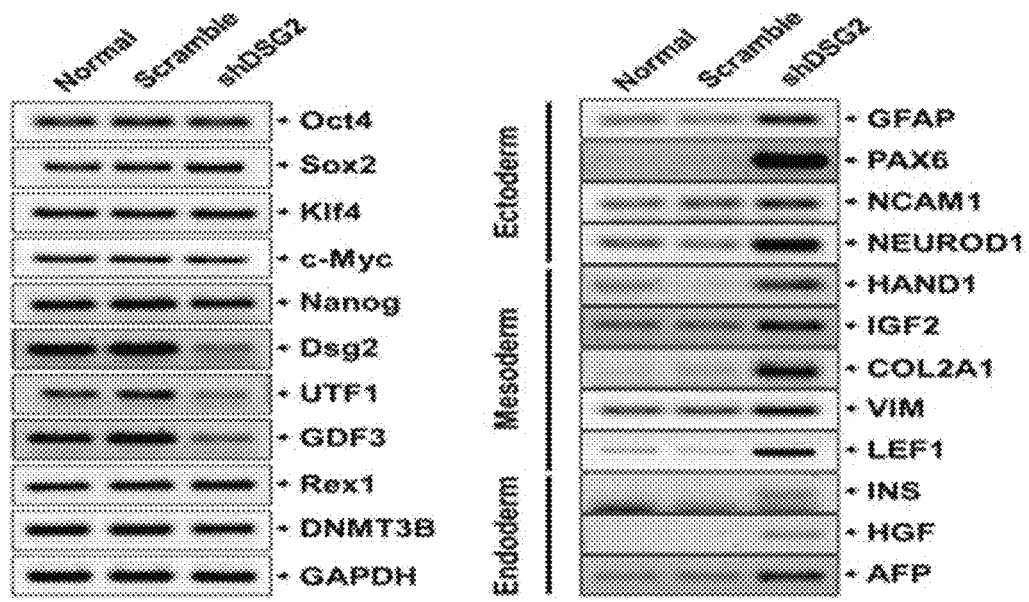

The PCR product was electrophoresed on 1% agarose gel. As a result, the expressions of the essential transcription factors for the undifferentiated human pluripotent stem cells such as UTF1 and GDF3 were reduced. On the other hand, the expressions of the genes playing an important role in the development of ectoderm, mesoderm, and endoderm were increased (FIG. 12C).

Figure 12D:
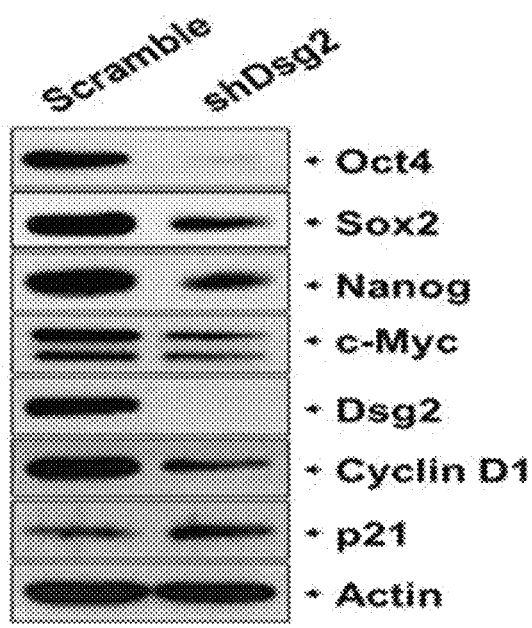

To investigate the difference in the expression of the undifferentiation marker between the scrambled cells and the shDsg2 cells, Western blotting was performed with Oct4, Sox2, Nanog, and c-Myc. As a result, the expressions of Oct4, Sox2, Nanog, and c-Myc were reduced in the shDsg2 cells. The down-regulation of Cyclin D1, a key factor for cell cycle and the up-regulation of p21 functioning to arrest cell cycle were also confirmed (FIG. 12D). Therefore, it was confirmed that the expression of Dsg2 played an important role in maintaining the undifferentiation status of human pluripotent stem cells.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for detecting undifferentiated human pluripotent stem cells comprising the step of measuring levels of Desmoglein 2 protein in separated human pluripotent stem cells,
   wherein the measurement of Desmoglein 2 protein levels comprises reacting human pluripotent stem cells with a Dsg2 protein specific antibody to form an antigen-antibody complex and measuring the antigen-antibody complex,
   wherein the antibody comprises a heavy chain variable region (VH) comprising the heavy chain CDR1 represented by SEQ. ID. NO: 60, the heavy chain CDR2 represented by SEQ. ID. NO: 61, and the heavy chain CDR3 represented by SEQ. ID. NO: 62; and a light chain variable region (VL) comprising the light chain CDR1 represented by SEQ. ID. NO: 64, the light chain CDR2 represented by SEQ. ID. NO: 65, and the light chain CDR3 represented by SEQ. ID. NO: 66.

2. A method for separating undifferentiated human pluripotent stem cells comprising the following steps:
   (a) reacting human pluripotent stem cells with an agent specifically binding to Desmoglein 2 protein; and
   (b) separating the human pluripotent stem cells that have been conjugated with said agent,
   wherein the agent specifically binding to Desmoglein 2 protein in step (a) is a Dsg2 specific antibody comprising a heavy chain variable region (VH) comprising the heavy chain CDR1 represented by SEQ. ID. NO: 60, the heavy chain CDR2 represented by SEQ. ID. NO: 61, and the heavy chain CDR3 represented by SEQ. ID. NO: 62; and a light chain variable region (VL) comprising the light chain CDR1 represented by SEQ. ID. NO: 64, the light chain CDR2 represented by SEQ. ID. NO: 65, and the light chain CDR3 represented by SEQ. ID. NO: 66.

3. A monoclonal antibody specifically binding to Desmoglein 2 having a heavy chain variable region ($V_H$) comprising the heavy chain CDR1 represented by SEQ. ID. NO: 60, the heavy chain CDR2 represented by SEQ. ID. NO: 61, and the heavy chain CDR3 represented by SEQ. ID. NO: 62; and a light chain variable region ($V_L$) comprising the light chain CDR1 represented by SEQ. ID. NO: 64, the light chain CDR2 represented by SEQ. ID. NO: 65, and the light chain CDR3 represented by SEQ. ID. NO: 66.

4. The method of claim 1 wherein measuring the antigen-antibody complex is performed using a western blot, ELISA (enzyme linked immunosorbent assay), immunoprecipitation assay, complement fixation assay, radio-immuno assay (RIA), immunodiffusion assay, protein chip assay, immunohisto staining, flow cytometry, or combinations thereof.

5. The method of claim 1 wherein the separating step is performed using an ELISA (enzyme linked immunosorbent assay), immunoprecipitation assay, complement fixation assay, radio-immuno assay (RIA), immunodiffusion assay, protein chip assay, flow cytometry, or combinations thereof.

* * * * *

SEQUENCE LISTING

<160> NUMBER OF SEQ ID NOS: 68

<210> SEQ ID NO 1
<211> LENGTH: 20
<212> TYPE: DNA
<213> ORGANISM: Artificial
<220> FEATURE:
<223> OTHER INFORMATION: Forward primer for Nanog

<400> SEQUENCE: 1
tgcctcacac ggagactgtc                    20

<210> SEQ ID NO 2
<211> LENGTH: 20
<212> TYPE: DNA
<213> ORGANISM: Artificial
<220> FEATURE:
<223> OTHER INFORMATION: Reverse primer for Nanog

<400> SEQUENCE: 2
tgctattctt cggccagttg                    20

<210> SEQ ID NO 3
<211> LENGTH: 20
<212> TYPE: DNA
<213> ORGANISM: Artificial

```
<220> FEATURE:
<223> OTHER INFORMATION: Forward primer for Oct4

<400> SEQUENCE: 3
cgaccatctg ccgctttgag                                               20

<210> SEQ ID NO 4
<211> LENGTH: 20
<212> TYPE: DNA
<213> ORGANISM: Artificial
<220> FEATURE:
<223> OTHER INFORMATION: Reverse primer for Oct4

<400> SEQUENCE: 4 cccctgtcc cccattccta                                                20

<210> SEQ ID NO 5
<211> LENGTH: 20
<212> TYPE: DNA
<213> ORGANISM: Artificial
<220> FEATURE:
<223> OTHER INFORMATION: Forward primer for Sox2

<400> SEQUENCE: 5
tacctcttcc tcccactcca                                               20

<210> SEQ ID NO 6
<211> LENGTH: 20
<212> TYPE: DNA
<213> ORGANISM: Artificial
<220> FEATURE:
<223> OTHER INFORMATION: Reverse primer for Sox2

<400> SEQUENCE: 6
actctcctct tttgcacccc                                               20

<210> SEQ ID NO 7
<211> LENGTH: 23
<212> TYPE: DNA
<213> ORGANISM: Artificial
<220> FEATURE:
<223> OTHER INFORMATION: Forward primer for Dsg2

<400> SEQUENCE: 7
aggtatggcc aaggaagcca cga                                           23

<210> SEQ ID NO 8
<211> LENGTH: 22
<212> TYPE: DNA
<213> ORGANISM: Artificial
<220> FEATURE:
<223> OTHER INFORMATION: Reverse primer for Dsg2

<400> SEQUENCE: 8
atagcgcctg tggcccctgt aa                                            22

<210> SEQ ID NO 9
<211> LENGTH: 23
<212> TYPE: DNA
<213> ORGANISM: Artificial
<220> FEATURE:
<223> OTHER INFORMATION: Forward primer for Pax6

<400> SEQUENCE: 9
aacagacaca gccctcacaa aca                                           23
```

<210> SEQ ID NO 10
<211> LENGTH: 23
<212> TYPE: DNA
<213> ORGANISM: Artificial
<220> FEATURE:
<223> OTHER INFORMATION: Reverse primer for Pax6

<400> SEQUENCE: 10
cgggaacttg aactggaact gac                                           23

<210> SEQ ID NO 11
<211> LENGTH: 20
<212> TYPE: DNA
<213> ORGANISM: Artificial
<220> FEATURE:
<223> OTHER INFORMATION: Forward primer for CD34

<400> SEQUENCE: 11
tgaagcctag cctgtcacct                                               20

<210> SEQ ID NO 12
<211> LENGTH: 20
<212> TYPE: DNA
<213> ORGANISM: Artificial
<220> FEATURE:
<223> OTHER INFORMATION: Reverse primer for CD34

<400> SEQUENCE: 12
cgcacagctg gaggtcttat                                               20

<210> SEQ ID NO 13
<211> LENGTH: 21
<212> TYPE: DNA
<213> ORGANISM: Artificial
<220> FEATURE:
<223> OTHER INFORMATION: Forward primer for AFP

<400> SEQUENCE: 13
ccatgtacat gagcactgtt g                                             21

<210> SEQ ID NO 14
<211> LENGTH: 21
<212> TYPE: DNA
<213> ORGANISM: Artificial
<220> FEATURE:
<223> OTHER INFORMATION: Reverse primer for AFP

<400> SEQUENCE: 14
ctccaataac tcctggtatc c                                             21

<210> SEQ ID NO 15
<211> LENGTH: 20
<212> TYPE: DNA
<213> ORGANISM: Artificial
<220> FEATURE:
<223> OTHER INFORMATION: Forward primer for hGAPDH

<400> SEQUENCE: 15
accacagtcc atgccatcac                                               20

<210> SEQ ID NO 16
<211> LENGTH: 20
<212> TYPE: DNA
<213> ORGANISM: Artificial
<220> FEATURE:
<223> OTHER INFORMATION: Reverse primer for hGAPDH

<400> SEQUENCE: 16
tccaccaccc tgttgctgta					20

<210> SEQ ID NO 17
<211> LENGTH: 19
<212> TYPE: DNA
<213> ORGANISM: Artificial
<220> FEATURE:
<223> OTHER INFORMATION: Forward primer for mActin

<400> SEQUENCE: 17
aggcccagag caagagagg					19

<210> SEQ ID NO 18
<211> LENGTH: 20
<212> TYPE: DNA
<213> ORGANISM: Artificial
<220> FEATURE:
<223> OTHER INFORMATION: Reverse primer for mActin

<400> SEQUENCE: 18
tacatggctg gggtgttgaa					20

<210> SEQ ID NO 19
<211> LENGTH: 20
<212> TYPE: DNA
<213> ORGANISM: Artificial
<220> FEATURE:
<223> OTHER INFORMATION: Forward primer for Klf4

<400> SEQUENCE: 19
tgtgattacg cgggctgcgg					20

<210> SEQ ID NO 20
<211> LENGTH: 20
<212> TYPE: DNA
<213> ORGANISM: Artificial
<220> FEATURE:
<223> OTHER INFORMATION: Reverse primer for Klf4

<400> SEQUENCE: 20
ggcggtgccc cgtgtgttta					20

<210> SEQ ID NO 21
<211> LENGTH: 20
<212> TYPE: DNA
<213> ORGANISM: Artificial
<220> FEATURE:
<223> OTHER INFORMATION: Forward primer for c-Myc

<400> SEQUENCE: 21
cccaggtcct cggacaccga					20

<210> SEQ ID NO 22
<211> LENGTH: 22
<212> TYPE: DNA
<213> ORGANISM: Artificial
<220> FEATURE:
<223> OTHER INFORMATION: Reverse primer for c-Myc

<400> SEQUENCE: 22
tgctcctctg cttggacgga ca					22

<210> SEQ ID NO 23

```
<211> LENGTH: 18
<212> TYPE: DNA
<213> ORGANISM: Artificial
<220> FEATURE:
<223> OTHER INFORMATION: Forward primer for UTF1

<400> SEQUENCE: 23
accagctgct gaccttga                                                    18

<210> SEQ ID NO 24
<211> LENGTH: 18
<212> TYPE: DNA
<213> ORGANISM: Artificial
<220> FEATURE:
<223> OTHER INFORMATION: Reverse primer for UTF1

<400> SEQUENCE: 24
ctggagaggg gagactgg                                                    18

<210> SEQ ID NO 25
<211> LENGTH: 20
<212> TYPE: DNA
<213> ORGANISM: Artificial
<220> FEATURE:
<223> OTHER INFORMATION: Forward primer for GDF3

<400> SEQUENCE: 25
tggtgactct caaccctgat                                                  20

<210> SEQ ID NO 26
<211> LENGTH: 20
<212> TYPE: DNA
<213> ORGANISM: Artificial
<220> FEATURE:
<223> OTHER INFORMATION: Reverse primer for GDF3

<400> SEQUENCE: 26
atggtcagtg agaagggaca                                                  20

<210> SEQ ID NO 27
<211> LENGTH: 24
<212> TYPE: DNA
<213> ORGANISM: Artificial
<220> FEATURE:
<223> OTHER INFORMATION: Forward primer for Rex1

<400> SEQUENCE: 27
cagatcctaa acagctcgca gaat                                             24

<210> SEQ ID NO 28
<211> LENGTH: 23
<212> TYPE: DNA
<213> ORGANISM: Artificial
<220> FEATURE:
<223> OTHER INFORMATION: Reverse primer for Rex1

<400> SEQUENCE: 28
gcgtacgcaa attaaagtcc aga                                              23

<210> SEQ ID NO 29
<211> LENGTH: 25
<212> TYPE: DNA
<213> ORGANISM: Artificial
<220> FEATURE:
<223> OTHER INFORMATION: Forward primer for DNMT3B

<400> SEQUENCE: 29
```

```
tgctgctcac agggcccgat acttc                                            25

<210> SEQ ID NO 30
<211> LENGTH: 28
<212> TYPE: DNA
<213> ORGANISM: Artificial
<220> FEATURE:
<223> OTHER INFORMATION: Reverse primer for DNMT3B

<400> SEQUENCE: 30
tcctttcgag ctcagtgcac cacaaaac                                         28

<210> SEQ ID NO 31
<211> LENGTH: 19
<212> TYPE: DNA
<213> ORGANISM: Artificial
<220> FEATURE:
<223> OTHER INFORMATION: Forward primer for GFAP

<400> SEQUENCE: 31
cctctccctg gctcgaatg                                                   19

<210> SEQ ID NO 32
<211> LENGTH: 22
<212> TYPE: DNA
<213> ORGANISM: Artificial
<220> FEATURE:
<223> OTHER INFORMATION: Reverse primer for GFAP

<400> SEQUENCE: 32
ggaagcgaac cttctcgatg ta                                               22

<210> SEQ ID NO 33
<211> LENGTH: 21
<212> TYPE: DNA
<213> ORGANISM: Artificial
<220> FEATURE:
<223> OTHER INFORMATION: Forward primer for NCAM1

<400> SEQUENCE: 33
acggaggagg agaggacccc a                                                21

<210> SEQ ID NO 34
<211> LENGTH: 23
<212> TYPE: DNA
<213> ORGANISM: Artificial
<220> FEATURE:
<223> OTHER INFORMATION: Reverse primer for NCAM1

<400> SEQUENCE: 34
cgttctcctt tgtctgtgtg gcg                                              23

<210> SEQ ID NO 35
<211> LENGTH: 21
<212> TYPE: DNA
<213> ORGANISM: Artificial
<220> FEATURE:
<223> OTHER INFORMATION: Forward primer for NEUROD1

<400> SEQUENCE: 35
gcagcgctgg agcccttctt c                                                21

<210> SEQ ID NO 36
<211> LENGTH: 19
<212> TYPE: DNA
```

```
<213> ORGANISM: Artificial
<220> FEATURE:
<223> OTHER INFORMATION: Reverse primer for NEUROD1

<400> SEQUENCE: 36
gatccgtggc tttgggccc                                              19

<210> SEQ ID NO 37
<211> LENGTH: 20
<212> TYPE: DNA
<213> ORGANISM: Artificial
<220> FEATURE:
<223> OTHER INFORMATION: Forward primer for HAND1

<400> SEQUENCE: 37 tccctttcc gcttgctctc                                              20

<210> SEQ ID NO 38
<211> LENGTH: 20
<212> TYPE: DNA
<213> ORGANISM: Artificial
<220> FEATURE:
<223> OTHER INFORMATION: Reverse primer for HAND1

<400> SEQUENCE: 38
catcgcctac ctgatggacg                                             20

<210> SEQ ID NO 39
<211> LENGTH: 20
<212> TYPE: DNA
<213> ORGANISM: Artificial
<220> FEATURE:
<223> OTHER INFORMATION: Forward primer for IGF2

<400> SEQUENCE: 39
ccccagatac cccgtgggca                                             20

<210> SEQ ID NO 40
<211> LENGTH: 20
<212> TYPE: DNA
<213> ORGANISM: Artificial
<220> FEATURE:
<223> OTHER INFORMATION: Reverse primer for IGF2

<400> SEQUENCE: 40
ggcggggtct tgggtgggta                                             20

<210> SEQ ID NO 41
<211> LENGTH: 20
<212> TYPE: DNA
<213> ORGANISM: Artificial
<220> FEATURE:
<223> OTHER INFORMATION: Forward primer for COL2A1

<400> SEQUENCE: 41
ggagatccgg gcagagggca                                             20

<210> SEQ ID NO 42
<211> LENGTH: 20
<212> TYPE: DNA
<213> ORGANISM: Artificial
<220> FEATURE:
<223> OTHER INFORMATION: Reverse primer for COL2A1

<400> SEQUENCE: 42
ccgaattcct gctcgggccc                                             20
```

<210> SEQ ID NO 43
<211> LENGTH: 20
<212> TYPE: DNA
<213> ORGANISM: Artificial
<220> FEATURE:
<223> OTHER INFORMATION: Forward primer for VIM

<400> SEQUENCE: 43
gagaactttg ccgttgaagc                                         20

<210> SEQ ID NO 44
<211> LENGTH: 20
<212> TYPE: DNA
<213> ORGANISM: Artificial
<220> FEATURE:
<223> OTHER INFORMATION: Reverse primer for VIM

<400> SEQUENCE: 44
tccagcagct tcctgtaggt                                         20

<210> SEQ ID NO 45
<211> LENGTH: 20
<212> TYPE: DNA
<213> ORGANISM: Artificial
<220> FEATURE:
<223> OTHER INFORMATION: Forward primer for LEF1

<400> SEQUENCE: 45
cggacacgag gtggccagac                                         20

<210> SEQ ID NO 46
<211> LENGTH: 20
<212> TYPE: DNA
<213> ORGANISM: Artificial
<220> FEATURE:
<223> OTHER INFORMATION: Reverse primer for LEF1

<400> SEQUENCE: 46
accgcatggg atggctgcac                                         20

<210> SEQ ID NO 47
<211> LENGTH: 19
<212> TYPE: DNA
<213> ORGANISM: Artificial
<220> FEATURE:
<223> OTHER INFORMATION: Forward primer for INS

<400> SEQUENCE: 47
aagcgtggca ttgtggaac                                          19

<210> SEQ ID NO 48
<211> LENGTH: 22
<212> TYPE: DNA
<213> ORGANISM: Artificial
<220> FEATURE:
<223> OTHER INFORMATION: Reverse primer for INS

<400> SEQUENCE: 48
ggctttattc catctctctc gg                                      22

<210> SEQ ID NO 49
<211> LENGTH: 20
<212> TYPE: DNA
<213> ORGANISM: Artificial
<220> FEATURE:

<223> OTHER INFORMATION: Forward primer for HGF

<400> SEQUENCE: 49
gcatcaaatg tcagccctgg                                         20

<210> SEQ ID NO 50
<211> LENGTH: 20
<212> TYPE: DNA
<213> ORGANISM: Artificial
<220> FEATURE:
<223> OTHER INFORMATION: Reverse primer for HGF

<400> SEQUENCE: 50
caacgctgac atggaattcc                                         20

<210> SEQ ID NO 51
<211> LENGTH: 27
<212> TYPE: DNA
<213> ORGANISM: Artificial
<220> FEATURE:
<223> OTHER INFORMATION: Primer for cloning heavy chain

<400> SEQUENCE: 51
atagacagat ggggtgtcg ttttggc                                  27

<210> SEQ ID NO 52
<211> LENGTH: 20
<212> TYPE: DNA
<213> ORGANISM: Artificial
<220> FEATURE:
<223> OTHER INFORMATION: Primer 5'MH1
<220> FEATURE:
<221> NAME/KEY: misc_feature
<222> LOCATION: (6)..(6)
<223> OTHER INFORMATION: n is a, c, g, or t

<400> SEQUENCE: 52
sargtnmagc tgsagsagtc                                         20

<210> SEQ ID NO 53
<211> LENGTH: 23
<212> TYPE: DNA
<213> ORGANISM: Artificial
<220> FEATURE:
<223> OTHER INFORMATION: Primer 5'MH2
<220> FEATURE:
<221> NAME/KEY: misc_feature
<222> LOCATION: (6)..(6)
<223> OTHER INFORMATION: n is a, c, g, or t

<400> SEQUENCE: 53
sargtnmagc tgsagsagtc wgg                                     23

<210> SEQ ID NO 54
<211> LENGTH: 24
<212> TYPE: DNA
<213> ORGANISM: Artificial
<220> FEATURE:
<223> OTHER INFORMATION: Primer for cloning light chain

<400> SEQUENCE: 54
ggatactaca gttggtgcag catc                                    24

<210> SEQ ID NO 55
<211> LENGTH: 24
<212> TYPE: DNA
<213> ORGANISM: Artificial

```
<220> FEATURE:
<223> OTHER INFORMATION: Primer 5'MK

<400> SEQUENCE: 55
gayattgtgm tsacmcarwc tmca                                          24

<210> SEQ ID NO 56
<211> LENGTH: 30
<212> TYPE: DNA
<213> ORGANISM: Artificial
<220> FEATURE:
<223> OTHER INFORMATION: Primer for light chain cloning

<400> SEQUENCE: 56
gacattgtgc tgacccaatc tccagcttct                                    30

<210> SEQ ID NO 57
<211> LENGTH: 24
<212> TYPE: DNA
<213> ORGANISM: Artificial
<220> FEATURE:
<223> OTHER INFORMATION: Primer for light chain cloning

<400> SEQUENCE: 57
gacattcagc tgacccagtc tcca                                          24

<210> SEQ ID NO 58
<211> LENGTH: 17
<212> TYPE: DNA
<213> ORGANISM: Artificial
<220> FEATURE:
<223> OTHER INFORMATION: M13 reverse primer

<400> SEQUENCE: 58
caggaaacag ctatgac                                                  17

<210> SEQ ID NO 59
<211> LENGTH: 127
<212> TYPE: PRT
<213> ORGANISM: Artificial
<220> FEATURE:
<223> OTHER INFORMATION: Heavy chain variable region of Ab 6-1

<400> SEQUENCE: 59

Gln Val Lys Leu Gln Glu Ser Gly Pro Glu Leu Val Arg Pro Gly Glu
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser Pro Ala Lys Thr Leu Glu Trp Leu
        35                  40                  45

Gly Val Ile Ser Ile Tyr Tyr Asp Asn Thr Asn Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Glu Gly Asp Tyr Phe Ala Leu Asp Tyr Trp Gly Gln Gly Thr
            100                 105                 110

Ser Val Thr Val Ser Ser Ala Lys Thr Thr Pro Pro Ser Val Tyr
        115                 120                 125

<210> SEQ ID NO 60
```

-continued

```
<211> LENGTH: 10
<212> TYPE: PRT
<213> ORGANISM: Artificial
<220> FEATURE:
<223> OTHER INFORMATION: hCDR1

<400> SEQUENCE: 60

Gly Tyr Thr Phe Thr Asp Tyr Ala Met His
1               5                   10

<210> SEQ ID NO 61
<211> LENGTH: 17
<212> TYPE: PRT
<213> ORGANISM: Artificial
<220> FEATURE:
<223> OTHER INFORMATION: hCDR2

<400> SEQUENCE: 61

Val Ile Ser Ile Tyr Tyr Asp Asn Thr Asn Tyr Asn Gln Lys Phe Lys
1               5                   10                  15

Gly

<210> SEQ ID NO 62
<211> LENGTH: 9
<212> TYPE: PRT
<213> ORGANISM: Artificial
<220> FEATURE:
<223> OTHER INFORMATION: hCDR3

<400> SEQUENCE: 62

Glu Gly Asp Tyr Phe Ala Leu Asp Tyr
1               5

<210> SEQ ID NO 63
<211> LENGTH: 115
<212> TYPE: PRT
<213> ORGANISM: Artificial
<220> FEATURE:
<223> OTHER INFORMATION: Light chain variable region of Ab 6-1

<400> SEQUENCE: 63

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Phe Pro Leu Thr
                85                  90                  95

Phe Gly Ala Gly Thr Lys Leu Glu Leu Lys Arg Ala Asp Ala Ala Pro
            100                 105                 110

Thr Val Ser
        115

<210> SEQ ID NO 64
<211> LENGTH: 8
<212> TYPE: PRT
<213> ORGANISM: Artificial
<220> FEATURE:
```

```
<223> OTHER INFORMATION: LCDR1

<400> SEQUENCE: 64

Ser Ala Ser Ser Ser Val Ser Tyr
1               5

<210> SEQ ID NO 65
<211> LENGTH: 7
<212> TYPE: PRT
<213> ORGANISM: Artificial
<220> FEATURE:
<223> OTHER INFORMATION: LCDR2

<400> SEQUENCE: 65

Asp Thr Ser Asn Leu Ala Ser
1               5

<210> SEQ ID NO 66
<211> LENGTH: 9
<212> TYPE: PRT
<213> ORGANISM: Artificial
<220> FEATURE:
<223> OTHER INFORMATION: LCDR3

<400> SEQUENCE: 66

Gln Gln Trp Ser Ser Phe Pro Leu Thr
1               5

<210> SEQ ID NO 67
<211> LENGTH: 381
<212> TYPE: DNA
<213> ORGANISM: Artificial
<220> FEATURE:
<223> OTHER INFORMATION: Heavy chain variable region of 6-1

<400> SEQUENCE: 67
caggttaagc tgcaggagtc tgggcctgag ctggtgaggc ctggggaatc agtgaagatt      60
tcctgcaagg gttccggcta cacattcact gattatgcta tgcactgggt gaagcagagt     120
cctgcaaaga ctctagagtg gcttggagtt attagtattt actatgataa tacaaactac     180
aaccagaaat ttaagggcaa ggccacattg actgttgaca atcctccag cacagcctat      240 atggaacttg ccagattgac atctgaggat tctgccatct attactgtgc aagagagggt     300
gactactttg ctttggacta ctggggtcaa ggaacctcag tcaccgtctc ctcagccaaa     360
acgacacccc catctgtcta t                                                381

<210> SEQ ID NO 68
<211> LENGTH: 345
<212> TYPE: DNA
<213> ORGANISM: Artificial
<220> FEATURE:
<223> OTHER INFORMATION: Light chain variable region of 6-1

<400> SEQUENCE: 68
gatattgtga tgacacagtc tccagcaatc atgtctgcat ctccagggga gaaggtcacc      60
atgacctgca gtgccagctc aagtgtaagt tacatgtact ggtaccagca gaagccagga    120
tcctccccca gactcctgat ttatgacaca tccaacctgg cttctggagt ccctgttcgc    180
ttcagtggca gtgggtctgg gacctcttac tctctcacaa tcagccgaat ggaggctgaa    240
gatgctgcca cttattactg ccagcaatgg agtagtttcc cgctcacgtt cggtgctggg    300
accaagctgg agctgaaacg ggctgatgct gcaccaactg tatcc                    345
```